(12) United States Patent
Garner

(10) Patent No.: US 12,251,513 B2
(45) Date of Patent: *Mar. 18, 2025

(54) DENTAL APPLIANCE APPARATUS AND RESPIRATION ENHANCEMENT

(71) Applicant: Dental Choice Holdings LLC, Louisville, KY (US)

(72) Inventor: Dena P. Garner, Isle of Palms, SC (US)

(73) Assignee: Dental Choice Holdings LLC, Louisville, KY (US)

( * ) Notice: Subject to any disclaimer, the term of this patent is extended or adjusted under 35 U.S.C. 154(b) by 291 days.

This patent is subject to a terminal disclaimer.

(21) Appl. No.: 17/545,434

(22) Filed: Dec. 8, 2021

(65) Prior Publication Data

US 2022/0096767 A1 Mar. 31, 2022

Related U.S. Application Data

(63) Continuation of application No. 16/406,324, filed on May 8, 2019, now Pat. No. 11,260,189, which is a
(Continued)

(51) Int. Cl.
*A61F 5/56* (2006.01)
*A61M 16/00* (2006.01)
(Continued)

(52) U.S. Cl.
CPC ........ *A61M 16/0493* (2014.02); *A61M 16/00* (2013.01); *A61F 5/566* (2013.01); *A62B 9/06* (2013.01)

(58) Field of Classification Search
CPC ...... A61F 5/566; A61F 5/56; A61F 2005/563; A61F 5/58; A61C 7/08; A61C 19/063;
(Continued)

(56) References Cited

U.S. PATENT DOCUMENTS

| 2,659,366 A | 11/1953 | Savarese |
| 3,124,129 A | 3/1964 | Grossberg |

(Continued)

FOREIGN PATENT DOCUMENTS

| CA | 2668913 A1 | 5/2008 |
| CN | 102123678 | 7/2011 |

(Continued)

OTHER PUBLICATIONS

Moses D.D.S., Allen J.; Evolution of Theory on Oral Appliances and Exercises for Sleep Apnea and Snoring; Sleep Diagnosis and Therapy, vol. 5 No. 7, Nov.-Dec. 2010.
(Continued)

*Primary Examiner* — Tarla R Patel
(74) *Attorney, Agent, or Firm* — Dinsmore & Shohl LLP

(57) ABSTRACT

A dental appliance apparatus is disclosed herein. In various aspects, the dental appliance may include a body removably attachable to one or more teeth selected from premolars and molars, and a flange extending forth from lingual portions of the body to contact a tongue at one or more locations proximate the premolars and the molars in order to cause a contraction of the genioglossus that positions the tongue anteriorly and downward toward the mandible by stimulation of the hypoglossal nerve. The dental appliance may include a connector connected to the body, and the connector may pass about buccal-labial sides of the anterior teeth. A bumper may be included on a labial side of the connector, and the bumper may contact the lips to promote pursed lips breathing. An anterior flange may extend lingually from the connector to stimulate the hypoglossal nerve proximate a tip of the tongue in order to cause contraction of the genioglossus to position the tongue anteriorly and downward toward the mandible.

18 Claims, 7 Drawing Sheets

Related U.S. Application Data continuation of application No. 14/993,198, filed on Jan. 12, 2016, now Pat. No. 10,328,225.

(60) Provisional application No. 62/244,107, filed on Oct. 20, 2015.

(51) Int. Cl.
*A61M 16/04* (2006.01)
*A62B 9/06* (2006.01)

(58) Field of Classification Search
CPC ... A61B 5/4547; A61B 5/4552; A61B 5/4557; A61B 5/682; A61B 5/0534; A63B 71/085; A63B 2071/086; A63B 2017/088
See application file for complete search history.

(56) References Cited

U.S. PATENT DOCUMENTS

| | | |
|---|---|---|
| 3,496,936 A | 2/1970 | Gores |
| 3,924,638 A | 12/1975 | Mann |
| 4,519,386 A | 5/1985 | Sullivan |
| 4,955,393 A | 9/1990 | Adell |
| 5,052,409 A | 10/1991 | Tepper |
| 5,194,003 A | 3/1993 | Garay et al. |
| 5,316,020 A | 5/1994 | Truffer |
| 5,406,963 A | 4/1995 | Adell |
| 5,536,168 A | 7/1996 | Bourke |
| 5,584,687 A | 12/1996 | Sullivan |
| 5,718,575 A | 2/1998 | Cross, III |
| 5,752,822 A * | 5/1998 | Robson ............... A61F 5/566 128/860 |
| 5,865,619 A | 2/1999 | Cross, III et al. |
| 5,879,155 A | 3/1999 | Kittelsen |
| 6,012,919 A | 1/2000 | Cross, III et al. |
| 6,092,524 A | 7/2000 | Barnes |
| 6,196,840 B1 | 3/2001 | Zentz et al. |
| 6,237,601 B1 | 5/2001 | Kittelsen et al. |
| 6,241,518 B1 | 6/2001 | Sullivan |
| 6,257,239 B1 | 7/2001 | Kittelsen et al. |
| 6,371,758 B1 | 4/2002 | Kittelsen |
| 6,415,794 B1 | 7/2002 | Kittelsen et al. |
| 6,467,484 B1 | 10/2002 | De Voss |
| 6,491,036 B2 | 12/2002 | Cook |
| 6,505,626 B2 | 1/2003 | Kittelsen et al. |
| 6,505,627 B2 | 1/2003 | Kittelsen et al. |
| 6,505,628 B2 | 1/2003 | Kittelsen et al. |
| 6,508,251 B2 | 1/2003 | Kittelsen et al. |
| 6,510,853 B1 | 1/2003 | Kittelsen et al. |
| 6,533,943 B1 | 4/2003 | Kittelsen et al. |
| 6,553,996 B2 | 4/2003 | Kittelsen et al. |
| 6,581,604 B2 | 6/2003 | Cook |
| 6,588,430 B2 | 7/2003 | Kittelsen et al. |
| 6,598,365 B2 | 7/2003 | Abraham et al. |
| 6,598,605 B1 | 7/2003 | Kittelsen et al. |
| 6,626,180 B1 | 9/2003 | Kittelsen |
| 6,675,806 B2 | 1/2004 | Kittelsen et al. |
| 6,675,807 B2 | 1/2004 | Kittelsen et al. |
| 6,691,710 B2 | 2/2004 | Kittelsen et al. |
| D496,154 S | 9/2004 | Herman et al. |
| D496,498 S | 9/2004 | Kittelsen et al. |
| D496,499 S | 9/2004 | Kittelsen |
| 6,820,623 B2 | 11/2004 | Cook |
| 6,830,051 B1 | 12/2004 | Lesniak |
| D500,897 S | 1/2005 | Herman |
| D500,898 S | 1/2005 | Herman |
| D501,062 S | 1/2005 | Herman |
| 6,837,246 B1 | 1/2005 | DeLuke |
| D502,995 S | 3/2005 | Cook |
| 6,941,952 B1 | 9/2005 | Rush, III |
| 7,059,332 B2 | 6/2006 | Eli |
| 7,299,804 B2 | 11/2007 | Kittelsen et al. |
| D570,724 S | 6/2008 | Kittelsen |
| D586,252 S | 2/2009 | Kittelsen |
| 7,549,423 B1 | 6/2009 | Hirshberg |
| 7,798,149 B2 | 9/2010 | Haduong |
| 7,890,193 B2 | 2/2011 | Tingey |
| 7,950,394 B2 | 5/2011 | Elkin |
| D641,478 S | 7/2011 | Belvedere et al. |
| 7,975,701 B2 | 7/2011 | Bergersen |
| 8,074,658 B2 | 12/2011 | Kittelsen et al. |
| 8,075,309 B2 | 12/2011 | Li et al. |
| 8,113,206 B2 | 2/2012 | Roettger et al. |
| 8,474,462 B2 | 7/2013 | Makower |
| 8,567,408 B2 | 10/2013 | Roettger et al. |
| 8,667,972 B2 | 3/2014 | Makkar et al. |
| 8,689,797 B2 | 4/2014 | Elkin |
| 8,839,795 B2 | 9/2014 | Von Arx |
| 9,022,903 B2 | 5/2015 | Rafih et al. |
| 9,138,376 B2 | 9/2015 | Allen |
| D743,108 S | 11/2015 | Charlton |
| D743,109 S | 11/2015 | Charlton |
| 9,668,827 B2 | 6/2017 | Roettger et al. |
| 9,968,419 B2 | 5/2018 | Alvarez et al. |
| 10,328,225 B2 * | 6/2019 | Garner ............ A61M 16/0493 |
| 11,083,956 B1 | 8/2021 | Varga |
| 11,129,746 B2 | 9/2021 | Alvarez |
| 11,260,189 B2 * | 3/2022 | Garner ................ A61M 16/00 |
| 11,266,802 B2 * | 3/2022 | Garner ............ A61M 16/0493 |
| 11,285,035 B2 | 3/2022 | Alvarez et al. |
| 2002/0066454 A1 | 6/2002 | Kittelsen et al. |
| 2002/0114694 A1 | 10/2002 | Kittelsen et al. |
| 2002/0144687 A1 | 10/2002 | Kittelsen et al. |
| 2002/0144688 A1 | 10/2002 | Kittelsen et al. |
| 2002/0144689 A1 | 10/2002 | Kittelsen et al. |
| 2002/0144690 A1 | 10/2002 | Kittelsen et al. |
| 2002/0144691 A1 | 10/2002 | Kittelsen et al. |
| 2002/0144692 A1 | 10/2002 | Kittelsen et al. |
| 2002/0144693 A1 | 10/2002 | Kittelsen et al. |
| 2002/0144695 A1 | 10/2002 | Cook |
| 2002/0192617 A1 | 12/2002 | Phan |
| 2003/0040679 A1 | 2/2003 | Weber et al. |
| 2003/0101999 A1 | 6/2003 | Kittelsen |
| 2004/0094165 A1 | 5/2004 | Cook |
| 2004/0107970 A1 | 6/2004 | Kittelsen et al. |
| 2004/0181166 A1 | 9/2004 | Williford et al. |
| 2004/0250817 A1 | 12/2004 | Kittelsen et al. |
| 2005/0115571 A1 | 6/2005 | Jacobs |
| 2005/0241646 A1 | 11/2005 | Sotos et al. |
| 2005/0284489 A1 | 12/2005 | Ambis |
| 2006/0078840 A1 | 4/2006 | Robson |
| 2006/0289013 A1 | 12/2006 | Keropian |
| 2007/0261701 A1 | 11/2007 | Sanders |
| 2007/0289600 A1 | 12/2007 | Li |
| 2008/0099029 A1 | 5/2008 | Lamberg |
| 2008/0138755 A1 | 6/2008 | Jansheski |
| 2008/0210244 A1 | 9/2008 | Keropian |
| 2009/0126742 A1 | 5/2009 | Summer |
| 2009/0130635 A1 | 5/2009 | Tortorici |
| 2009/0191502 A1 | 7/2009 | Cao et al. |
| 2009/0221884 A1 | 9/2009 | Ryan |
| 2009/0308403 A1 | 12/2009 | Roettger et al. |
| 2010/0147315 A1 | 6/2010 | Chodorow |
| 2010/0252053 A1 | 10/2010 | Garner et al. |
| 2010/0269836 A1 * | 10/2010 | Roettger ............ A63B 71/085 433/214 |
| 2011/0017221 A1 | 1/2011 | Garner et al. |
| 2011/0039223 A1 | 2/2011 | Li |
| 2011/0114100 A1 | 5/2011 | Ramiro et al. |
| 2012/0090625 A1 | 4/2012 | Evans et al. |
| 2012/0165862 A1 | 6/2012 | Allen |
| 2012/0305008 A1 | 12/2012 | Garner et al. |
| 2012/0325224 A1 | 12/2012 | Elkin |
| 2013/0042876 A1 | 2/2013 | Hermanson |
| 2013/0066236 A1 | 3/2013 | Herman |
| 2013/0068237 A1 | 3/2013 | Herman |
| 2013/0074851 A1 | 3/2013 | Herman |
| 2013/0081640 A1 | 4/2013 | Herman |
| 2013/0298916 A1 * | 11/2013 | Alvarez ................ A61C 5/90 264/16 |
| 2014/0026896 A1 | 1/2014 | Roettger et al. |
| 2014/0080083 A1 | 3/2014 | Mathieu |
| 2014/0090652 A1 | 4/2014 | Hakimi |

(56) References Cited

U.S. PATENT DOCUMENTS

| | | | |
|---|---|---|---|
| 2014/0135868 A1* | 5/2014 | Bashyam | A61N 1/3601 |
| | | | 607/42 |
| 2014/0272761 A1 | 9/2014 | Lowe | |
| 2015/0079530 A1 | 3/2015 | Bergersen | |
| 2015/0366636 A1 | 12/2015 | Zampino | |
| 2016/0230007 A1 | 8/2016 | Johnson | |
| 2016/0158628 A1 | 9/2016 | Layzell | |
| 2016/0367342 A1* | 12/2016 | Alvarez | A61C 8/0093 |
| 2017/0020716 A1 | 1/2017 | Hart et al. | |
| 2018/0207022 A1 | 7/2018 | Alvarez et al. | |
| 2018/0344508 A1 | 12/2018 | Brown | |
| 2018/0353838 A1 | 12/2018 | Padavan | |
| 2019/0262565 A1 | 8/2019 | Garner | |
| 2019/0374734 A1 | 12/2019 | Garner | |
| 2020/0261255 A1 | 8/2020 | Huang | |
| 2022/0008244 A1 | 1/2022 | Hart et al. | |
| 2022/0087854 A1 | 3/2022 | Knutzen | |
| 2022/0096767 A1 | 3/2022 | Garner | |
| 2023/0233923 A1 | 7/2023 | Garner | |

FOREIGN PATENT DOCUMENTS

| | | |
|---|---|---|
| DE | 29509294 | 5/1995 |
| DE | 102004009883 | 9/2005 |
| FR | 2872406 | 3/2007 |
| GB | 2444588 | 3/2009 |
| GB | 2513902 A | 11/2014 |
| JP | 2006519656 A | 8/2006 |
| JP | 2011514185 | 5/2011 |
| JP | 5008394 B2 | 8/2012 |
| JP | WO2014188517 | 2/2017 |
| JP | WO2014188517 A | 2/2017 |
| WO | 2009012243 | 1/2009 |
| WO | 2009128339 | 10/2009 |
| WO | 2009135210 | 11/2009 |
| WO | 2011153172 | 8/2011 |
| WO | 2011153173 | 8/2011 |
| WO | 2011153174 | 8/2011 |
| WO | 2011153175 | 8/2011 |

OTHER PUBLICATIONS

Fogel, Robert B., et al.; Within-Breath Control of Genioglossal Muscle Activation in Humans: Effect of Sleep-Wake State; The Journal of Physiology 550, 899-910; Aug. 1, 2003 (published online as of Jun. 13, 2003).

Garner, Dena P., The Effects of Mouthpiece Use on Gas Exchange Parameters During Steady-State in College-Aged Men and Woman, Journal of the American Dental Association 142(9), Sep. 2011.

Cheng, S., Movement of the Tongue During Normal Breathing in Awake, Healthy Humans, The Journal of Physiology 586, 4283-4294, Sep. 1, 2008 (published online as of Jul. 17, 2008).

U.S. Appl. No. 16/516,958, filed Jul. 19, 2019 titled "Single Arch Dental Device and Method of Manufacture".

Okeson; "Fundamentals of Occlusion and Temporomandibular Disorders" (The C. V. Mosby Company, St. Louis, 1985), p. 333-340.

Lucia; "Modern Gnathological Concepts—Updated" (Quintessence Publishing Co., Inc., Chicago, 1983), Chapters 2, 3, and 4 (pp. 29-63).

Shore; A Mandibular autorepositioning Appliance, JADA, vol. 75, Oct. 1967.

Shore, Nathan Allen, "Temporomandibular Joint Dysfunction and Occlusal Equilibration", J.B. Lippincott Compan, 1976 [Second Edition], Philadelphia, pp. 237-241.

Various Authors, Compendium of Continuing Education in Dentistry, 30(2) Aegis Publications LLC, 2009.

D.P. Garner & E.J. McDivitt, Effects of Mouthpiece Use on Lactate and Cortisol Levels During and After 30 Minutes of Treadmill Running, Open Access Journal of Science and Technology, vol. 3, Agial Publishing House, 2015.

D.P. Garner, Effects of Various Mouthpieces on Respiratory Physiology During Steady-State Exercise in College-Aged Subjects, Sports Dentistry & Mouthgards, Academy of General Dentistry, Nov./Dec. 2015.

A.J. Miller, Oral and Pharyngeal Reflexes in the Mammalian Nervous System: Their Diverse Range in Complexity and Theh Pivotal Role of the Tongue, Crit. Rev. Oral Biol. Med., Inern'l & American Assoc. for Dental Research, 13(5): 409-425, 2002.

J.P. Saboisky, B.J. Luu, J.E. Butler, S.C. Gandevia, Effects of Tongue Position and Lung Volume on Voluntary Mximal Tongue Protrusion Force in Humands, Respiratory Physiology & Neurobiology, Elsevier, Dec. 4, 2014.

J.E. Schmidt, C.R. Carlson, A.R. Usery, A.S. Quevedo, Effects of Tongue Position on Mandibular Muscle Activity and Heart Rate Function, Oral Surg. Oral Med. Oral Path. Oral Radiol. Endod, Mosby Inc., 108:881-888, 2009.

D.P. Gardner, W.D. Dudgeon, E.J. McDivitt, The Effects of Mouthpiece Use on Cortisol Levels During an Intense Bout of Resistance Exercise, J. of Strength and Conditioning Research, National Strench & Conditioning Assoc., 25(10), 2011.

Garner, Dudgeon, McDivitt and Scheett, The Effects of Mouthpiece Use on Gas Exchange Parameters During Steady-State Exercise in College-Aged Men and Women. J Am. Dent. Assoc., Am Dental Assoc., 142(9) 1041-1047, 2011.

Murakami, S., Maeda, Y., Ghanem, A., Uchiyama, Y., & Kreilborg, S. Influence of Mouthguard on Temporomandibular Joint. Scand J Med Sports, 18, 591-595 (2008).

Pae, A., Yoo, R., Noh, K, Pake, J., & Kwon, K. The Effects of Mouthguards on the Athletic Ability of Professional Golfers. DNEN Traumatol, John Wiley & Son, 29, 47-51 (2013).

U.S. Appl. No. 16/519,665, filed Jul. 23, 2019 titled "Methods of Respiratory Enhancement Using a Dental Appliance".

Freedman, George; The Dentist's Role in Sport Performance Mouthwear, Oral Health, Dec. 1, 2010 (https://www.oralhealthgroup.com/features/the-dentists-role-in-sport-performance-mouthwear).

www.underarmour.com; UA Performance Mouthwear (Year: 2009).

U.S. Appl. No. 16/406,324 filed May 8, 2019 titled "Dental Appliance Apparatus and Respiratory Enhancement".

U.S. Appl. No. 61/132,588, filed Jun. 19, 2008 titled Composite oral appliances and methods for manufacture.

USPTO; Non-Final Office Action issued in U.S. Appl. No. 17/580,835 mailed Sep. 13, 2024.

\* cited by examiner

DENTAL APPLIANCE APPARATUS AND RESPIRATION ENHANCEMENT

CROSS-REFERENCE TO RELATED APPLICATIONS

This continuation patent application claims priority to and benefit of, under 35 U.S.C. § 120, U.S. Continuation patent application Ser. No. 16/406,324, filed May 8, 2019 which claims priority to U.S. patent application Ser. No. 14/993,198, now issued as U.S. Pat. No. 10,328,225, filed Jan. 12, 2016, which claims priority and benefit of U.S. Provisional Patent Application No. 62/244,107 filed Oct. 20, 2015, all of which are hereby incorporated by reference in their entireties herein.

BACKGROUND OF THE INVENTION

Field

The present disclosure relates to dental appliances, and, in particular, to dental appliances that may enhance respiratory performance, for example, during physical activity.

Background

During engagement in a physical activity, the human body utilizes three pathways to create energy in the form of adenosine triphosphate (ATP). The body utilizes a mixture of both fats and carbohydrates to make ATP, with some minimal contributions from protein. However, despite the abundance of fat, the human body will fatigue during physical activity. One common cause of fatigue is the build-up of lactic acid, specifically the hydrogen ions associated with lactic acid build-up that interfere with producing ATP. Thus, reducing lactic acid build-up may reduce fatigue by reducing interference with the production of ATP, which may, for example, improve performance by increasing the duration or intensity of engagement in the physical activity.

Increasing carbon dioxide ($CO_2$) exhalation may reduce build-up of lactic acid, as $CO_2$ in solution acts as a buffer for hydrogen ions in the body. Increasing $O_2$ uptake may also reduce the buildup of lactic acid. Thus, respiratory performance improvement including increasing exhalation of $CO_2$ and increasing $O_2$ uptake may reduce fatigue by reducing lactic acid buildup that may result in improved performance.

Cortisol is a glucocorticosteroid hormone that affects various tissues and organs in the human body. Cortisol may aid the body in responding to stress by, for example, maintaining cardiovascular functions. However, prolonged or excessively high levels of cortisol may cause fatigue, reduce endurance, suppress the immune system, and have other deleterious physiological effects. For example, protein synthesis, which is necessary for repairing and increasing muscles, is important for recovery following engagement in physical activity. However, elevated levels of cortisol have been shown to inhibit protein synthesis. By limiting the ongoing rise in cortisol levels, performance may be improved.

Accordingly, there is a need for improved apparatus as well as related methods that reduce build-up of lactic acid and cortisol during engagement in physical activity.

BRIEF SUMMARY OF THE INVENTION

These and other needs and disadvantages may be overcome by the apparatus disclosed herein. Additional improvements and advantages may be recognized by those of ordinary skill in the art upon study of the present disclosure.

A dental appliance apparatus is disclosed herein. In various aspects, the dental appliance may include a body removably attachable to one or more teeth selected from premolars and molars, and a flange extending forth from lingual portions of the body to contact a tongue at one or more locations proximate the premolars and the molars in order to cause a contraction of the genioglossus that positions the tongue anteriorly and downward toward the mandible by stimulation of the hypoglossal nerve. The dental appliance may include a connector connected to the body, and the connector may pass about buccal-labial sides of the anterior teeth. A bumper may be included on a labial side of the connector, and the bumper may contact the lips to promote pursed lips breathing. An anterior flange may extend lingually from the connector to stimulate the hypoglossal nerve proximate a tongue tip of the tongue in order to cause contraction of the genioglossus that positions the tongue anteriorly and downward toward the mandible.

Related methods of use of the dental appliance may include the step of receiving a dental appliance within a mouth of a user, and may include the step of causing contraction of the genioglossus that positions the tongue anteriorly and downward toward the mandible by stimulating the hypoglossal nerve through contact of the hypoglossal nerve with more flanges that extend forth from lingual portions of the dental appliance. The hypoglossal nerve may be stimulated at various locations around the tongue including the side of the tongue and proximate the tip of the tongue, and flanges may be provided at various locations about the dental appliance to so stimulate the hypoglossal nerve by contact with the tongue.

This summary is presented to provide a basic understanding of some aspects of the apparatus and methods disclosed herein as a prelude to the detailed description that follows below. Accordingly, this summary is not intended to identify key elements of the apparatus and methods disclosed herein or to delineate the scope thereof.

Figure 1A:
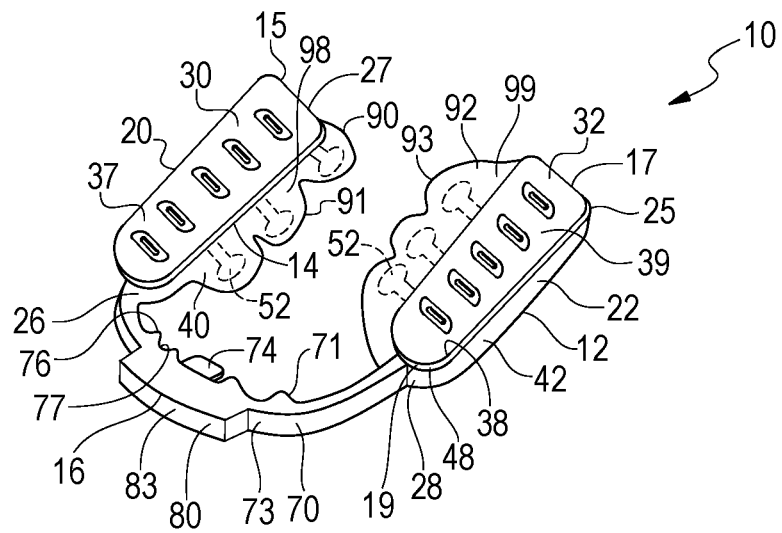
FIG. 1A illustrates by top frontal perspective view an exemplary implementation of a dental appliance.

The Figures are exemplary only, and the implementations illustrated therein are selected to facilitate explanation. The number, position, relationship and dimensions of the elements shown in the Figures to form the various implementations described herein, as well as dimensions and dimensional proportions to conform to specific force, weight, strength, flow and similar requirements are explained herein or are understandable to a person of ordinary skill in the art upon study of this disclosure. Where used in the various Figures, the same numerals designate the same or similar elements. Furthermore, when the terms "top," "bottom," "right," "left," "forward," "rear," "first," "second," "inside," "outside," and similar terms are used, the terms should be understood in reference to the orientation of the implementations shown in the drawings and are utilized to facilitate description thereof. Use herein of relative terms such as generally, about, approximately, essentially, may be indicative of engineering, manufacturing, or scientific tolerances such as ±0.1%, ±1%, ±2.5%, ±5%, or other such tolerances, as would be recognized by those of ordinary skill in the art upon study of this disclosure.

DETAILED DESCRIPTION OF THE INVENTION

The dental appliance disclosed herein, in various aspects, may be removably attached to at least a portion of the teeth of the user. The dental appliance disclosed herein, in various aspects, may enhance respiratory performance of the user by interaction with various anatomical features of the mouth, jaw, or face, and, thus, increase athletic performance of the user. In various aspects, the dental appliance may afford protection to the teeth, tongue, lips, mandible, or other anatomical features of the mouth, jaw, or face.

The design of the dental appliance, in various aspects, is such that, when the dental appliance is positioned in the mouth, with the individual biting down, the dental appliance stimulates the hypoglossal nerve (XII cranial nerve) causing the genioglossus (tongue protruding muscle) to protrude/contract in a forward motion. This forward contraction of the genioglossus results in an increased oropharynx opening in the throat (Garner, D. P. and McDivitt, E., Effects of mouthpiece use on airways openings and lactate levels in healthy college males. Compendium: A Supplement of Continuing Education in Dentistry, 30(2): 9-13 (2009) and Garner, D. P., Effects of various mouthpieces on respiratory physiology during steady state exercise in college-aged subjects. Gen Dent, 63, 30-34 (2015).

Thus, when a user starts exercising, he/she should breathe through the mouth, while biting down on the mouthpiece. This may result in a type of pursed lip breathing which has been shown to lower ventilation, while improving oxygen and carbon dioxide kinetics and lactate levels during and after endurance exercise. While exercising anaerobically (specifically resistance exercise), the user should clench down and breathe through his/her mouth. This has been shown to decrease cortisol levels post exercise (see study by Garner, Dudgeon, McDivitt and Scheett, The effects of mouthpiece use on gas exchange parameters during steady-state exercise in college-aged men and women. J Am. Dent. Assoc. 2011 142(9) 1041-1047 and Garner, D. P., Dudgeon, W. D., and McDivitt, E., The effects of mouthpiece use on cortisol levels during an intense bout of resistance exercise. Journal of Strength and Conditioning, 25(10): 2866-2871 (2011).

As used herein, ventilation is the measure of air into and out of the lunges, and respiratory rate is the measure of the exchange of oxygen and carbon dioxide within the lungs. Specifically, ventilation is the defined as the liters per minute. Respiratory rate is defined herein as breaths per minute. Tidal volume is defined herein as the volume of air inhaled and exhaled during one breath.

Anterior, as used herein, refers to portions of the mouth proximate the front of the mouth for example, proximate the lips or the front incisors. Posterior, as used herein, refers to the back of the mouth, for example, proximate the 3rd molar (if present) or the pharynx. Mesial, as used here, refers to the midline of the mouth. The central incisors are usually located on either side of the mesial line or midline. For example, a structure that extends mesially may extend toward the mesial line or midline, and a structure that is positioned mesially may be positioned about the mesial line or midline. Axial, as used herein, refers to directions along a vertical axis of the body as, for example, generally defined by the spinal column.

The tongue is a complex collection of muscles and nerves that may be stimulated in various ways either directly or indirectly by the dental appliance. The tongue muscles may be divided functionally into protruder muscles that move the tongue blade in the anterior direction and retractor muscles that pull the tongue in the posterior direction toward the posterior pharyngeal wall. Protruder muscles include the extrinsic genioglossus, the intrinsic verticalis and transversus muscles. Retractor muscles include the extrinsic hyoglossus and styloglossus, and the intrinsic inferior and superior longitudinalis muscles. Stimulation of both the genioglossus and hyoglossus may cause depression of the tongue.

The tongue muscles are innervated by branches of the hypoglossal nerve, which is the twelfth cranial nerve. The hypoglossal nerve trunk bifurcates into large mesial and lateral branches as the hypoglossal nerve approaches the tongue muscles, with the mesial branch containing axons supplying the protruder muscles (both intrinsic and extrinsic muscles) and the lateral branch the retractors.

The hypoglossal motor nucleus receives both excitatory and inhibitory synaptic input from many brain regions. Direct inputs originate in the nucleus of the solitary tract, the majority of the reticular nuclei, the principal and spinal trigeminal nuclei, reticularis subcoeruleus, the caudal Raphe nucleus, and the Kolliker-Fuse nucleus. These regions, in turn, receive substantia nigra, the superior colliculus, and the mesencephalic trigeminal nucleus. Many of these regions modulate ventilatory drive, with the reticular formation containing the interneurons that link the central respiratory drive from the pre-Botzinger complex with the hypoglossal motor nucleus. Accordingly, the tongue including the tongue muscles may be connected to respiratory performance through the hypoglossal nerve, so that respiratory performance may be increased by stimulating the tongue or positioning the tongue in certain positions. Increased respiratory performance may reduce fatigue by reducing lactic acid formation, and increased respiratory performance may reduce cortisol levels, which may promote muscle healing and have other beneficial effect.

For example, pursing of the lips appears to correlate with contraction of the genioglossus including expansions or contractions of other tongue muscles thereby positioning the tongue anteriorly and downward toward the mandible. When engaging in pursed lips breathing, the subject purses their lips while breathing in and breathing out slowly. There are two types of pursed lips breathing with one being a decrease in respiratory rate and an increase in tidal volume and the other type of pursed lips breathing being one with a decrease in respiratory rate with no change in tidal volume. It has been found that subjects with chronic obstructive pulmonary disease (COPD) experienced a subsequent and significant reduction in respiratory rate with faster recovery when subjects with COPD practiced pursed lip breathing while exercising, so that pursed lips breathing may be associated with increased respiratory performance.

As noted above, pursed lip breathing may be correlated with the contraction of the genioglossus. Studies of the genioglossus have found that contraction of the genioglossus may cause dilation of the pharyngeal airway. Particularly, when the genioglossus is contracted (i.e. the tongue is pushed down toward the mandible and forward toward the anterior teeth), there is a subsequent relaxation of the pharyngeal area in the back of the throat. Thus, pursed lips breathing may cause contraction of the genioglossus muscle that, in turn, causes dilation of the pharyngeal airway, resulting in the observed increased respiratory performance with pursed lips breathing. Thus, a dental appliance that promotes pursed lips breathing may increase respiratory performance.

In addition, stimulation of the hypoglossal nerve at various locations by the dental appliance may cause contraction of the genioglossus that positions the tongue down and anteriorly thereby resulting in dilation of the pharyngeal airway and concomitant increased respiratory performance. Various stimulations of the hypoglossal nerve by the dental appliance may otherwise signal various other nerves, nuclei, or regions of the brain that may produce various physiological effects that increase respiratory performance. Genioglossus may include the genioglossus as well as other protruder and retractor muscles, and contraction of the genioglossus may include movement of the other protruder muscles or movement of the retractor muscles, as would be readily understood by those of ordinary skill in the art upon study of this disclosure.

A forward shift of the mandible such as may occur with the dental appliance implementations disclosed herein may increase the pharyngeal area. Applicant has found airway anatomical differences with various implementations of the dental appliance, specifically measuring the diameter and width of the oropharynx with computed tomography (CT) scans that demonstrated a 9% improvement in both the diameter and width when subjects used the dental appliance. (See Garner, D. P. and McDivitt, E., Effects of mouthpiece use on airways openings and lactate levels in healthy college males. Compendium: A Supplement of Continuing Education in Dentistry, 30(2): 9-13 (2009)). Although the mandibular displacement of that implementation of the dental appliance was not as pronounced as those with a sleep apneic device, a significant effect on oropharynx width occurred when using the dental appliance.

Finally, it was found that implementations of the dental appliance that allowed subjects to clench all their teeth evenly with vertical displacement and a level pressure distribution between all teeth resulted in increased respiratory performance.

In various aspects, the dental appliance may comprise two bodies received on either side of the mouth with the two bodies connected to one another by a connector. The bodies may be constructed of a plurality of material layers bonded or otherwise secured to one another in various ways. In general, the body portions of the dental appliance may be composed of one or more layers of materials. These materials may include ethyl-vinyl acetate (EVA); thermoplastic polyolefin, various ethylene-based elastomers; various hydrocarbon resins (which are may be combined with EVA, thermoplastic polyolefin, or various ethylene-based elastomers), polycaprolactone (which may be combined with EVA), low-density polyethylene, high density poly-ethylene, polycarbonate and/or various polymers, laminates and other materials that will be recognized by those skilled in the art upon review of the present disclosure. In certain aspects, the composite material may be a pre-laminated sheet including a layer of polycarbonate bound to a layer of polyester urethane which is available under the trade name Durasoft® from the Scheu Dental Co. located in Iserlohn, Germany. Typically, these materials may be selected with a durometer (hardness) of between about 70 A to about 96 A or between about 55 D and about 90 D.

As described herein, in various aspects, one of the material layers of the plurality of material layers is a bite pad, and another of the material layers is an occlusal pad. Various other material layer(s) may be interposed between the bite pad and the occlusal pad, and additional material layer(s) may be placed about the occlusal pad or about the bite pad, in various aspects. The dental appliance may be constructed, at least in part, of the bite pad bonded to the occlusal pad, and the bite pad with the occlusal pad bonded thereto forms at least a portion of the dental appliance. In various aspects, the bite pad may support the occlusal pad, may interact with other elements of the dental appliance, and may confer various mechanical properties upon the dental appliance. The bite pad may interact with the teeth, and, thus, may be configured with treads including other tooth grippable surface, and the bite pad may have a selected hardness as indicated, for example, by a Shore hardness value as measured by a durometer. In various aspects, the occlusal pad may engage the user's teeth to attach removably the dental appliance thereto, and the occlusal pad may be custom fitted to engage the user's teeth. The occlusal pad may have a selected hardness as indicated, for example, by a Shore hardness value.

The bite pad is composed of one or more bite pad materials. In various aspects, the bite pad material may include a mixture of styrene block copolymer and ethylene vinyl acetate (EVA). An exemplary styrene block copolymer is available as DYNAFLEX® part number G2782 from GLS Corporation, Thermoplastic Elastomers Division, 833 Ridgeview Dr., McHenry, Ill. 60050. EVA is available from a number of sources, such as the ELVAX® resins from Dupont Packaging and Industrial Polymers, 1007 Market Street, Wilmington, Del. 19898.

In various aspects, the bite pad material may include a mixture of a styrene block copolymer and a polyolefin elastomer. The polyolefin elastomer may be a copolymer of ethylene and octene-1. An exemplary copolymer is available as ENGAGE® from Dupont Canada, Inc., P.O. Box 2200, Streetsville, Mississauga, Ontario L5M 2H3.

The bite pad material may include, in various aspects, a mixture of a thermoplastic rubber, which includes thermoplastic elastomer and thermoplastic urethane, with a polyolefin elastomer. Exemplary thermoplastic rubbers are Santoprene® thermoplastic elastomer from Advanced Elastomer Systems, L. P., 388 South Main Street, Akron, Ohio 44311 and Kraton® thermoplastic elastomer from the Shell Oil Company, Houston, Tex. Kraton® includes astyrene-ethylenelbutylenes-styrene block copolymer. In various aspects, the bite pad material may include polypropylene part number AP6112-HS from Huntsman Corporation, Chesapeake, VA 23320. In various aspects, the bite pad material may include HD-6706 ESCORENE® Injection Molding Resin [a high density polyethylene] from ExxonMobil Chemical Company, P.O. Box 3272, Houston, TX.

The bite pad material of the bite pad, in various aspects, may have a durometer of at least 60 D to resist substantial deformation and retaining a substantially planar configuration between at least two cusps of the teeth of the user when the teeth of the user are clenched about the bite pad. In various aspects, the bite pad material of the bite pad may have a durometer of between about 60 D to about 90 D although this may vary. In some aspects, the bite pad material of the bite pad has a Shore A hardness of about 82.

The occlusal pad is composed of one or more occlusal pad materials. In various aspects, the occlusal pad material may be transformable between a pliable state and a non-pliable state. In the pliable state, the occlusal pad material of the occlusal pad may be shaped to conform to the teeth of the user. In the non-pliable state, the occlusal pad material of the occlusal pad generally retains its conformance to the teeth of the user as shaped when in the pliable state. In various aspects, the occlusal pad may be transformed between the pliable state and the non-pliable state by heating and cooling, respectively. For example, heating the occlusal pad material in warm water may allow the occlusal pad to be fitted to the user's teeth and, after having been fitted, the occlusal pad material may be cooled to the non-pliant state thereby capturing the fit of the user's teeth in the occlusal pad material. The occlusal pad material is transformed from the non-pliable state to the pliable state at a temperature tolerable by the user upon placement of the occlusal pad material in the pliable state within the user's mouth, in various aspects. The occlusal pad material may transform between the non-pliant and pliant state at a temperature greater than human body temperature but less than about 100° C., in various implementations.

In various aspects, the occlusal pad material of the occlusal pad includes a mixture of polycaprolactone. An exemplary polycaprolactone is Capra 6500 polycaprolactone from Perstorp, UK Limited, Warrington, Cheshire UK. In various aspects, the occlusal pad material of occlusal pad 40 includes a mixture of polycaprolactone and ethylene vinyl acetate (EVA) such as ELVAX®. In various aspects, the occlusal pad material of occlusal pad 40 includes ethylene vinyl acetate (EVA) alone, such as ELVAX®. In various aspects, the occlusal pad material of occlusal pad 40 includes a mixture of polycaprolactone and a polyolefin elastomer, and the polyolefin elastomer may be a copolymer of ethylene and octene-1. An exemplary copolymer is available as ENGAGE® from Dupont Canada, Inc., P.O. Box 2200, Streetsville, Mississauga, Ontario L5M 2H3.

Figure 1B:
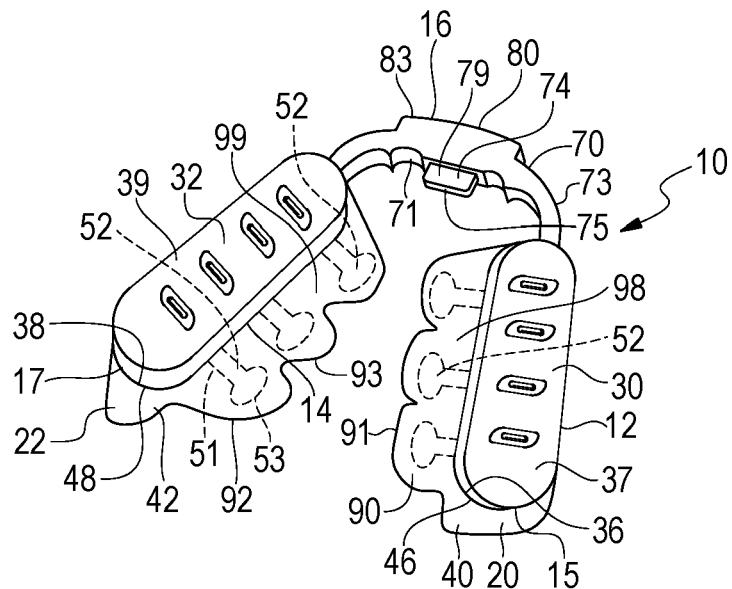
FIG. 1B illustrates by top rear perspective view the exemplary implementation of the dental appliance of FIG. 1A.
Figure 1C:
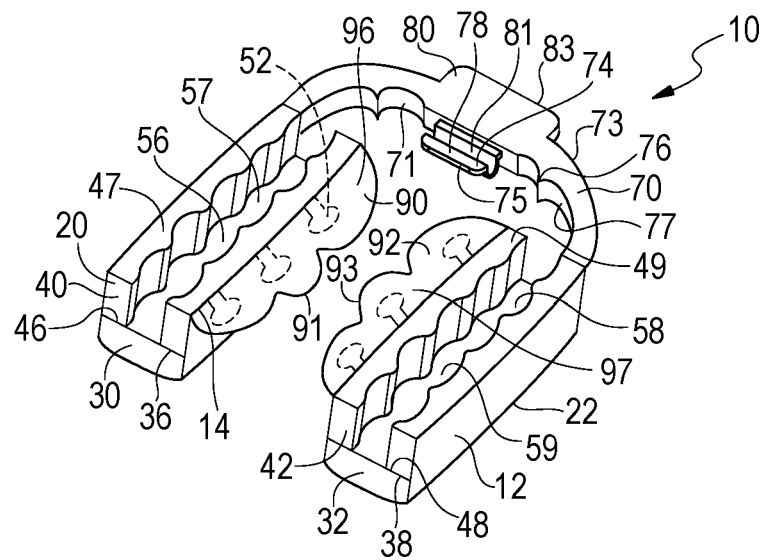
FIG. 1C illustrates by bottom perspective view the exemplary implementation of the dental appliance of FIG. 1A.

FIGS. 1A, 1B and 1C illustrate an exemplary implementation of a dental appliance 10. As illustrated in FIGS. 1A, 1B and 1C, exemplary dental appliance 10 includes bodies 20, 22 connected to one another by connector 70. The dental appliance 10, as illustrated in FIGS. 1A, 1B and 1C, is formed as a generally U-shaped member, the curved portions of the "U" extends around anterior portions of the user's mouth as anterior portion 16 of dental appliance 10, and the straight portions of the "U" extend from the anterior toward the posterior of the mouth with posterior ends 15, 17 of dental appliance 10. When dental appliance 10 is positioned in the mouth, dental appliance 10 defines a buccallabial side 12 that is generally oriented toward the cheeks and/or lips of the user and a lingual side 14 that is generally oriented toward the user's tongue. Anterior portion 16 of dental appliance 10 is positioned anteriorly mesially, as illustrated in the Figures, and posterior ends 15, 17 are positioned posteriorly in the mouth.

Connector 70 includes bumper 80, and occlusal pads 40, 42 include flanges 90, 92, in this implementation. Bodies 20, 22 of exemplary dental appliance 10 include occlusal pads 40, 42 bonded to bite pads 30, 32, respectively. As illustrated, side 46 of occlusal pad 40 is bonded to side 36 of bite pad 30 and side 48 of occlusal pad 42 is bonded to side 38 of bite pad 32. Sides 36, 38, are generally oriented opposite to sides 37, 39 of bite pads 30, 32, respectively, and sides 46, 48, are generally oriented opposite to sides 47, 49 of occlusal pads 40, 42, in this implementation.

Occlusal pads 40, 42 define occlusal pad channels 56, 58 in sides 47, 49, respectively, in this implementation. In exemplary dental appliance 10, occlusal pad channels 56, 58 may removably engage teeth on opposing sides of the mandible generally in the posterior portion of the mandible. For example, occlusal pad channels 56, 58 of dental appliance 10 engage the mandibular 1st bicuspid, mandibular 2nd bicuspid, mandibular 1st molar, mandibular 2nd molar, and mandibular 3rd molar on the right and left sides, respectively. Occlusal pad channels 56, 58 may be fit to the user's teeth in order to conform to the shape of the user's teeth including interstices between the user's teeth. Note that the mandibular 3rd molars (left and right; i.e. wisdom teeth) may be omitted from the illustrations and discussion herein for clarity of explanation and because the mandibular $3^{rd}$ molars are frequently absent.

The occlusal pad channels 56, 58 are elongated, as illustrated, and are generally oriented along the mesial-distal axis. The at least a portion of occlusal pad channels 56, 58 may extend over one or more of the canines, premolars and/or molars on each side of the mouth. The occlusal pad channels 56, 58 may be configured in shape of the teeth of the user. A channel occlusal surface 57, 59 of occlusal channels 56, 58, respectively, contacts at least a portion of the occlusal surface of the teeth. The channel occlusal surfaces 57, 59 may be configured to conform to a least a portion of the occlusal surface of the user's teeth and may be configured to conform to the surfaces of all the teeth received in the occlusal channels 56, 58. To conform, typically, cavities will be formed in the channel occlusal surfaces 57, 59 that correspond to at least the cusps of the occlusal surfaces of the teeth. In certain aspects, this may more evenly distribute the force from clenching or an impact over the occlusal surface of the teeth and, among other things, may also improve retention and fitment of dental appliance 10.

When occlusal pad cannels 56, 58 of occlusal pads 40, 42 are engaged with the teeth of the mandible, sides 47, 49 of occlusal pads 40, 42 are oriented toward the gum of the mandible and sides 37, 39 of bite pads 30, 32 are oriented toward teeth of the upper jaw. The teeth of the upper jaw may engage with sides 37, 39 of bite pads 30, 32, respectively. Sides 37, 39 of bite pads 30, 32 may include treads and so forth, and may otherwise be generally adapted to contact occlusal surfaces of posterior teeth of the upper jaw opposite to the mandibular teeth engaged with occlusal pad channels 56, 58 of occlusal pads 40, 42.

Bite pads 30, 32 may be of sufficient hardness to resist substantial penetration by the teeth and deformation as the teeth of the user are clenched about bite pads 30, 32. Bite pads 30, 32 may be formed from a material such as, for example, high density polyethylene or polypropylene that may have a durometer of between about 60 D to about 90 D.

As illustrated in FIGS. 1A, 1B, and 1C, body 20 and body 22 are connected to one another by connector 70, so that connector 70 secures body 20 and body 22 to one another. Connector 70 may be formed of a variety of materials including those materials set forth herein as being suitable for use in occlusal pads or of other materials or combinations of materials, as would be recognized by those of ordinary skill in the art upon study of this disclosure.

Connector 70 may be configured to extend as an arch around either the lingual side, labial side, or both the lingual side and labial side of the anterior teeth of the user, in various implementations. In certain implementations, connector 70 may extend along or just below the gum line on dental appliance 10, which is configured to be removably attached to the mandibular teeth.

Connector 70 and occlusal pads 40, 42 may be formed as a unitary structure in some implementations such that connector 70 extends between occlusal pads 40, 42, as illustrated. In other implementations, connector 70 and bite pads 30, 32 may be formed as a unitary structure, such that connector 70 extends between bite pads 30, 32. In still other implementations, connector 70 may be attached to bite pads 30, 32, occlusal pads 40, 42, or both bite pads 30, 32 and occlusal pads 40, 42 by, for example, various adhesives, mechanical connections, thermal bonding, and combinations thereof.

When dental appliance 10 is positioned in the mouth with occlusal pad channels 56, 58 engaged with posterior mandibular teeth, connector 70 generally passes about labial portions of the anterior mandibular teeth of the user with side 71 of connector 70 biased against the anterior mandibular teeth, and side 73 of connector 70 is oriented labially (i.e. toward the lips). Note that side 71 of connector 70 is fit to the user's teeth, in this implementation, so that side 71 conforms to the shape of the user's teeth including the interstices between the teeth.

As illustrated in FIGS. 1A, 1B and 1C, bumper 80 extends forth from side 73 of connector 70 generally mesially along connector 70. Bumper 80 may be formed of the same material as connector 70 so that connector 70 and bumper 80 form a unitary structure, in some implementations. In other implementations, bumper 80 may be secured to connector 70 by, for example, adhesive, mechanical connector(s), or thermal bond(s), and bumper 80 may be formed of various materials, as would be recognized by those of ordinary skill in the art upon study of this disclosure. In yet other implementations, bumper 80 may be removably attachable to connector 70 to allow the user to either attach bumper 80 to connector 70 or remove bumper 80 from connector 70 as the user may desire.

Flanges 90, 92 extend forth mesially from lingual side 14 of dental appliance generally along the straight portions of the "U," as illustrated in FIGS. 1A, 1B and 1C. Flange 90 extends mesially from body 20 with edge 91 of flange 90 being of a scalloped configuration, as illustrated. Similarly, as illustrated, flange 92 extends mesially from body 22 with edge 93 of flange 92 being of a scalloped configuration. When dental appliance 10 is engaged with the mandibular teeth, sides 98, 99 of flanges 90, 92 are oriented generally toward the palate, while sides 96, 97 of flanges 90, 92 are oriented generally toward the mandible. Flanges 90, 92 are oriented so that sides 98, 99 are set apart from the palate, in this implementation, resulting is no contact between flanges 90, 92 including sides 98, 99, respectively, and the palate when dental appliance 10 is engaged with the mandibular teeth.

As illustrated, flanges 90, 92 are somewhat wedge-shapes with the broad part of the wedge being where flanges 90, 92 emerge from lingual side 14 of dental appliance 10 and flanges 90, 92 then tapering to form edge 91, 93. In other implementations, flanges 90, 92 may be more planar in shape with generally constant thickness between sides 96, 98 and generally constant thickness between sides 97, 99. Flanges 90, 92 extend mesially a distance sufficient to impinge upon the side of the tongue thereby compressing portions of the genioglossus while avoiding creating a gag response, the distance being specific to the anatomy of the user, in various implementations.

Edges 91, 93 are formed along the side of flanges 90, 92 that extend furthest in the mesial lingual direction. Edges 91, 93 are sufficiently blunt (illustrated as being rounded but other implementations may have other shapes) so that edges 91, 93 do not injure the tongue. The axial dimension of edge 91, 93 is less than the axial dimension of bases 20, 22 as given, for example, by the length between side 39 and side 49 or the length between lingual body edge 133 and side 39.

Flanges 90, 92 are exemplary, and flange as used herein may include protuberances, extensions, or structures that extend forth from the lingual side of the dental appliance and are configured to touch the tongue in order to stimulate the hypoglossal nerve of the tongue, for example, by compression of the genioglossus including other muscles or tissues of the tongue. The flanges 90, 92 may stimulate the hypoglossal nerve by touching portions of the tongue enervated by thy hypoglossal nerve such as portions of the tongue along the side of the tongue. Flanges, such as flanges 90, 92, may have other shapes in other implementations. Edges 91, 93 are exemplary, and edge as used herein may include portions of the flange that generally contact the tongue to stimulate the hypoglossal nerve.

The implementation of dental appliance 10 includes supports 52 (illustrated in phantom) that are imbedded within flanges 90, 92 to support structurally flanges 90, 92. Flanges 90, 92 may be of unitary construction with the occlusal pads 40, 42, so that flanges 90, 92 are formed of the same material as occlusal pads 40, 42 and molded around supports 52. Supports 52, in this implementation are cantilevered from bite pads 30, 32 with support ends 51 of supports 52 secured to bite pads 30, 32. Supports 52 may be of unitary construction with bite pads 30, 32, or support ends 51 of supports 52 may be attached to bite pads 30, 32, for example, by adhesive. Supports 52 have a "T" shape at support ends 53, but may have, for example, a "Y" shape, or other shape or combination of shapes, in other implementations. Various numbers of supports 52 may be included in various implementations of dental appliance 10, or, in some implementations, supports 52 may be omitted entirely. In other implementations, flanges, such as flanges 90, 92, may extend lingually mesially from bite pads, such as bite pads 30, 32, and may be formed of the same material as the bite pads, or flanges may extend forth from other portions of a lingual side of a dental appliance, such as lingual side 14 of dental appliance 10.

Figure 2:
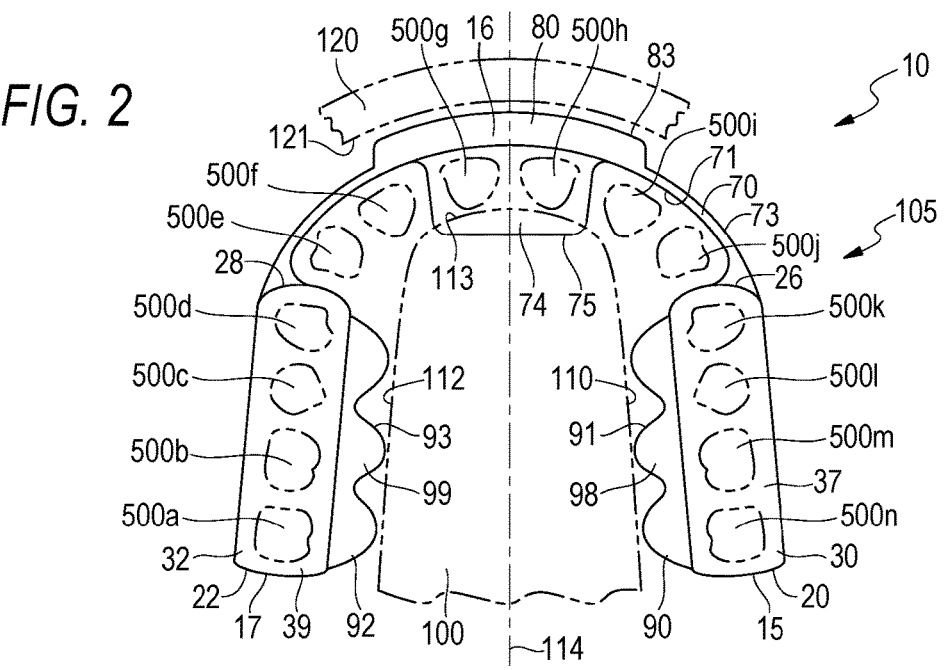
FIG. 2 illustrates by plan view the exemplary implementation of the dental appliance of FIG. 1A in engagement with the mandibular teeth.

FIG. 2 illustrates dental appliance 10 received in the mouth and engaged with the mandibular teeth 105 of the user. As illustrated in FIG. 2, tooth 500a, 500b, 500c, 500d, 500e, 500f, 500g are the left mandibular 2nd molar, left mandibular 1st molar, left mandibular $2^{11c1}$ bicuspid, left mandibular 1st bicuspid, left mandibular cuspid, left mandibular lateral incisor, left mandibular central incisor, respectively. Tooth 500h, 500i, 500j, 500k, 500l, 500m, 500n, are the right mandibular central incisor, right mandibular lateral incisor, right mandibular cuspid, right mandibular 1st bicuspid, right mandibular 2nd bicuspid, right mandibular 1st molar, right mandibular 2nd molar, respectively, as illustrated in FIG. 2.

As illustrated in FIG. 2, edge 91 of flange 90 is biased against at least portions of side 110 of the portion of the tongue 100 generally adjacent teeth 500k, 500l, 500m, 500n on the right side of the mandible when body 20 of dental appliance 10 is engaged with the mandibular teeth. Edge 93 of flange 92, as illustrated in FIG. 2, is biased against portions of side 112 of the portion of the tongue 100 generally adjacent teeth 500a, 500b, 500c, 500d on the left side of the mandible when body 22 of dental appliance 10 is engaged with the mandibular teeth.

The biasing of edges 91, 93 of flanges 90, 92 against at least portions of sides 110, 112, respectively, of tongue 100 may compresses the genioglossus along the side of the tongue or may otherwise physically touch the tongue to stimulate the hypoglossal nerve. Stimulation of the hypoglossal nerve by flanges 90, 92 may cause contraction of the genioglossus that positions the tongue 100 anteriorly and lowered toward the mandible, which may result in dilation of the pharyngeal airway and, thus, increased respiratory performance. Scalloped edges 91, 93, as illustrated, may be more effective in stimulating the hypoglossal nerve than straight edges, as, for example, the scalloped edges may differentially compress the genioglossus or otherwise differentially stimulate the tongue. For example, peaks of the scallop shape may compress the genioglossus while the valleys of the scallop shape may compress the genioglossus a lesser amount than the peaks or may avoid compressing the genioglossus altogether. Edges, such as edges 91, 93, may have waved, straight, saw-tooth, or other configurations or combinations of configurations, in other implementations.

Occlusal pad channels 56, 58 of bodies 20, 22 engage teeth 500k, 500l, 500m, 500n on the right side and teeth 500a, 500b, 500c, 500d on the left side, respectively, as illustrated in FIG. 2. Posterior ends 15, 17 of bodies 20, 22 are generally positioned posteriorly coincident with teeth 500n, 500a on the right and left side, respectively, as illustrated, and anterior portion 16 is positioned anteriorly about mesial line 114. Anterior ends 26, 28 of bodies 20, 22 are positioned at or posterior to tooth 500k, 500d, respectively, when dental appliance 10 is received in the mouth of a user, as illustrated.

Note that the mandibular 3rd molars (left and right; (i.e. wisdom teeth) are omitted from FIG. 2 both for clarity of explanation and because the mandibular 3rd molars are frequently absent. It should be understood that occlusal pad channels 56, 58 of dental appliance 10 may engage the mandibular 3rd molars when the mandibular $3^{rd}$ molar(s) are present. Flanges 90, 92 may generally extend in the anterior-posterior direction from the mandibular Pt bicuspid to the mandibular $3^{rd}$ molar when, for example, the mandibular $3^{rd}$ molars are present) or flanges 90, 92 may generally extend in the anterior-posterior direction from the mandibular Pt bicuspid to the mandibular $2^{rd}$ molar, for example, when the mandibular $3^{rd}$ molar is absent. In various implementations, flanges 90, 92 may extend in the anterior-posterior direction adjacent at least portions of one or more teeth selected from the mandibular 2nd molar 500a, 500n, mandibular Pt molar 500b, 500m, mandibular 2nd bicuspid 500c, 500l, mandibular Pt bicuspid 500d, 500k. In various implementations, edges 91, 93 may extend in the anterior-posterior direction adjacent at least portions of one or more teeth selected from the mandibular 2nd molar 500a, 500n, mandibular Pt molar 500b, 500m, mandibular $2^{nd}$ bicuspid 500c, 500l, mandibular Pt bicuspid 500d, 500k.

Connector 70 generally passes about buccal-labial portions of the anterior mandibular teeth of the user with side 71 of connector 70 biased against the anterior mandibular teeth, for example teeth 500e, 500f, 500g, 500h, 500i, 500j, and side 73 of connector 70 is oriented labially (i.e. toward the lips), as illustrated in FIG. 2. Side 71 of connector 70, as illustrated in FIG. 2, is biased against the mandibular cuspid, the mandibular lateral incisor, and the mandibular central incisor on both the left and right sides.

As illustrated in FIG. 2, side 83 of bumper 80 is biased against interior side 121 of lower lip 120 proximate mesial line 114. Bumper 80 does not intrude between the lips but merely biases against the interior side 121 of lower lip 120 so that bumper 80 remains entirely within the mouth cavity. The biasing of bumper 80 against the lower lip 120 (and the upper lip in some implementations) stimulates the lower lip 120 (or both lips) causing the lips to purse. Bumper 80 may assume various shapes that promote the pursing of the lips. Pursing of the lips in response to stimulation by bumper 80 may cause contraction of the genioglossus thereby positioning the tongue 100 anteriorly and lowered toward the mandible, which may result in dilation of the pharyngeal airway and, thus, increased respiratory performance.

Portions of connector 70 extend posteriorly from lingual side 66 of tooth 62 to form anterior flange 74 with posterior end 75. Anterior flange 74 may extend a distance T from the centerline of tooth 62 to posterior end 75, as illustrated in FIG. 3C, with tooth 62 selected, for example, from tooth 500e, 500f, 500g, 500h, 500i, 500j. Posterior end 75 is positioned to engage portions of the tongue 100 proximate tongue tip 113 in order to stimulate tongue 100, as illustrated in FIGS. 2 and 3C. Tongue tip 113 in the illustration is located generally along labial portions of tongue 100, for example, along teeth 500e, 500f, 500g, 500h, 500i, 500j. Anterior flange 74 may be mesially symmetric, and anterior flange 74 may extend along connector 70, for example, from the tooth 500e to tooth 500j, from tooth 500f to tooth 500i, or from tooth 500g to tooth 500h, in various implementations.

Engagement of anterior flange 74 including posterior end 75 or side 78 with portions of the tongue 100 proximate tongue tip 113 as well as the position of anterior flange 74 with respect to connector 70 may cause contraction of the genioglossus, and may, by the location of side 78, position the tongue 100 anteriorly and lowered toward the mandible, which may result in dilation of the pharyngeal airway and, thus, increased respiratory performance.

It should be noted that stimulation of the lip(s), such as lip 120, by bumper 80 and contraction of the genioglossus caused by stimulation of tongue 100 at various locations by flanges 74, 90, 92 all potentially implicate stimulation of the hypoglossal nerve including the trigeminal nerve (fifth cranial nerve), and various portions of the brain in communication with the hypoglossal nerve or the trigeminal nerve that may be associated with respiration. Thus, such stimulation of the tongue at various locations by flanges 74, 90, 92 as well as pursed lips breathing as provoked by bumper 80 may increase respiratory performance is other ways that may or may not be known at present.

Figure 3A:
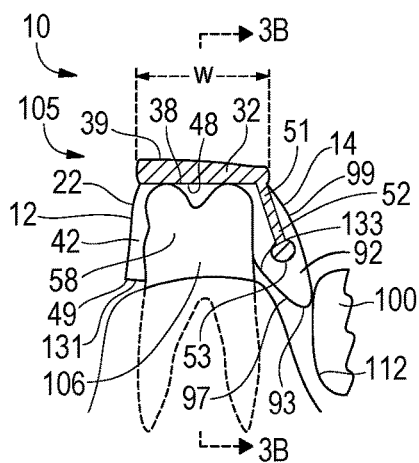
FIG. 3A illustrates by cross-sectional view portions of the exemplary implementation of the dental appliance of FIG. 1A in engagement with a mandibular tooth.

FIG. 3A illustrates body 22 of dental appliance 10 engaged with mandibular tooth 106, where mandibular tooth 106 may be selected, for example, from tooth 500a, 500b, 500c, 500d. As illustrated in FIG. 3A, body 22 includes bite pad 32, occlusal pad 42, and flange 92. Bite pad 32 is secured to occlusal pad 42, and mandibular teeth, such as teeth 500a, 500b, 500c, 500d, are received in occlusal channel 58 of occlusal pad 42, as illustrated. While FIGS. 3A and 3B and the attendant discussion are directed toward body 22 of dental appliance 10 for explanatory purposes, it should be recognized that body 20 of dental appliance 10 may be configured similarly to body 22 of dental appliance 10. Also, while body 20, 22 of exemplary dental appliance 10 includes bite pads, 30, 32 bonded to occlusal pads 40, 42, respectively, it should be recognized that bite pads 30, 32 or occlusal pads 40, 42 may be comprised of multiple layers of materials. It should be further recognized that body 20, 22 may include additional layer(s) of material(s) or combinations of materials that may impart various mechanical functionalities to bodies 20, 22. It should also be recognized that bite pads 30, 32 and occlusal pads 40, 42 may be of the same material to form a unitary structure, in certain implementations.

When the teeth are engaged in the occlusal channel 58 of dental appliance 10, a buccal body edge 131 of body 22 is positioned above the gum line of the user, as illustrated. In other implementations, buccal body edge 131 may extend below the gum-line of the user, or portions of buccal body edge 131 may be above the gum-line while other portions of buccal body edge 131 may extend below the gum-line. In some implementations, the buccal body edge 131 may be generally proximate the occlusal surface of the teeth so that the buccal side of occlusal channel 58 is either de minimis or omitted entirely.

Similarly, lingual body edge 133 may be variously positioned above the gum-line, as illustrated. Lingual body edge 133 may extend below the gum-line or portions of lingual body edge 133 may be above the gum-line while other portions of lingual body edge 133 may extend below the gum-line, in various implementations. In some implementations, the lingual body edge 133 may be generally proximate the occlusal surface of the teeth so that the lingual side of channel 58 is either de minimis or omitted entirely.

Flange 92, as illustrated, is of generally unitary construction with occlusal pad 42, and support 52 is cantilevered from bite pad 32 to support flange 92. Support end 51 of support 52 is attached to bite pad 32, and support end 53 of support 52 has a "T" configuration, as illustrated, and support 52 lies internally within flange 92. Edge 93 of flange 92 may be biased against the side 112 of the portion of the tongue 100, for example, from about tooth 500a to tooth 500d. In other implementations, flange 92 may be of generally unitary construction with occlusal pad 42, or flange 92 may be of unitary construction with one or more other layers interposed between bite pad 32 and occlusal pad 42.

Figure 3B:
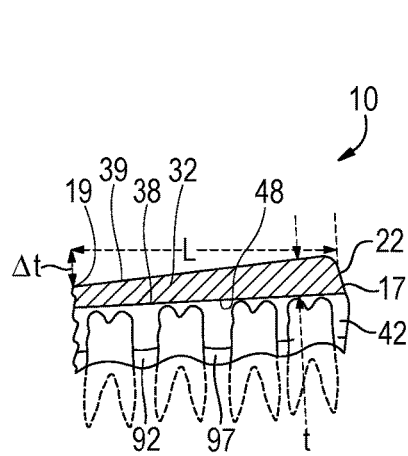
FIG. 3B illustrates by cross-sectional view portions of the exemplary implementation of the dental appliance of FIG. 1A in engagement with mandibular teeth.
Figure 3C:
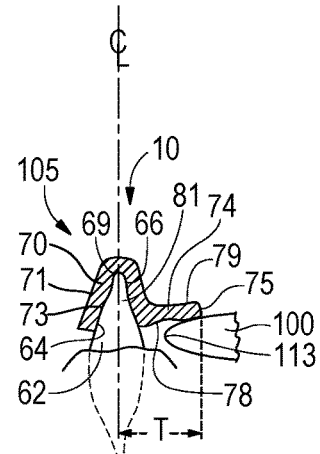
FIG. 3C illustrates by cross-sectional view portions of the exemplary implementation of the dental appliance of FIG. 1A in engagement with an anterior mandibular tooth.

As illustrated in FIG. 3B, body 22 is engaged with tooth 500a, 500b, 500c, 500d. From a top view (see FIGS. 1A, 1B), bite pads 30, 32 may have an oblong shape, a generally rectangular shape, a kidney shape, an oval shape, an egg shape or be otherwise shaped to extend along at least a portion of an occlusal surfaces of the teeth engaged with occlusal pad channels 56, 58 and the opposing maxillary teeth. The bite pads 30, 32 are generally configured to space the occlusal surfaces of opposing teeth when a clenching force is exerted on bodies 20, 22 including bite pads 30, 32 by the user.

As illustrated in FIG. 3A, the width W of bite pad 32 may be selected to contact or otherwise provide support between opposing teeth. The width W may be either constant or variable along the length L of bite pad 32, in various implementations. The width W of bite pad 32 may be at least as wide as the distance between the cusps of individual adjacent teeth and the cusps of the opposing maxillary teeth. In certain aspects, the width W may be as wide or wider than the width of the adjacent teeth or at least as wide as the spacing of the cusps of the teeth. Width W may range, for example, between about 5 mm and about 15 mm.

As illustrated in FIG. 3B, the length L of the bite pad 32 is selected so that bite pad 32 extends along the teeth engaged with body 22. Length L may range from about 10 millimeters to about 25 millimeters, in various implementations.

The thickness t from the occlusal surface of a tooth, such as tooth 106, to side 39 of bite pad 32, as illustrated in FIGS. 3A, 3B, generally establishes the distance the mandibular teeth will remain separated from corresponding maxillary teeth when the jaw is clenched or when the jaw receives an impact while dental appliance 10 is attached. The thickness t may be generally equivalent to the thickness of bite pad 32, in various implementations.

As illustrated in FIG. 3B, thickness t generally decreases by zlt from posterior end 17 to anterior end 19 to define a slope $\Delta t/L$. In various implementations, the slope, $\Delta t/L$ may range from $1/100 \leq z lt/L \leq 1/20$ In some implementations, the slope may be about $\Delta t/L$ 0 meaning no slope or generally constant thickness t along length L.

The thickness t may vary from about 1 mm to about 2 mm, in some implementations. In various implementations, thickness t may be generally about 5 mm at posterior end 17 and about 4 mm at anterior end 19. Thickness t may be generally in the range of about 2 mm to about 6 mm at proximal end 17 and thickness t may be generally in the range of about 1 mm to about 4 mm at anterior end 19. Most specifically, the thickness t may range approximately from 1.7 mm to 2.2 mm, while the thickness t at the anterior end 19 to side 39 of bite pad 32 at the anterior end 19 may range between approximately 0.7 mm to 1.2 mm. In some implementations, the thickness t may approach 0.00 millimeters (e.g. an edge) at the anterior end 19. In various implementations, the bite pads slope, for example with 1 mm anterior end 19 increasing gradually in slope to 2 mm posterior end 17. Note that, in implementations without a bite pad, such as bite pad 32, length L, width W, thickness t, and slope $\Delta t/L$ may be defined in reference to such implementations in ways as would be readily recognized by those of ordinary skill in the art upon study of this disclosure.

The slope At/L may enhance forward protrusion of the mandible (jaw) due to the biting down on these bite pads, the lack of material on the backside of the front bottom teeth, and the material on the inside of the dental appliance which aids in pushing the tongue in and forward, in such implementations.

The bite pads 30,32 elevate and create a minimal opening so that the individual may clench on the dental appliance and breathe through the mouth. If the thickness t too large, dental appliance 10 may not properly stimulate the hypoglossal nerve in ways that result in a pushing down and forward motion of the tongue, so that the dental appliance 10 fails to function properly. If the thickness t too large, a pressing down of the tongue by dental appliance 10 may not occur. In various other implementations, the thickness t may be between about 0.25 millimeter and about 2.5 millimeters. Bite pads 30, 32 may have a constant thickness with respect to length, a varying thickness with respect to length, or either a constant or varying thickness along the width.

The effects of dental appliance 10 use on respiratory performance may be related, at least in part, to the even contact between occlusal surfaces and bite pads 30, 32, which may be promoted by the slope At/L. The slope At/L may allow all teeth to contact bite pads 30, 32 equally at maximal intercuspal positions. Laboratory results seem to indicate that differences in the evenness of contact between teeth, along with varying vertical dimensions have resulted in different outcomes (Garner, 2015). (See: Murakami, S., Maeda, Y., Ghanem, A., Uchiyama, Y., & Kreilborg, S. Influence of mouthguard on temporomandibular joint. Scand J Med Sports, 18, 591-595 (2008); Pae, A., Yoo, R., Noh, K, Pake, J., & Kwon, K The effects of mouthguards on the athletic ability of professional golfers. Dent Traumatol, 29, 47-51 (2013))

For example, the slope of bite pad 32, as illustrated in FIG. 3B, along with a similar slope of bite pad 30 may cause a forward displacement of the mandible that may improve respiratory performance by increasing the pharyngeal area. In particular, the slope of bite pads 30, 32 may allow all the teeth in contact with bodies 20, 22 to be clenched more or less evenly with minimal vertical displacement between the mandibular teeth and the maxillary teeth. This may release the temporal mandibular joint allowing more forward displacement of the mandible resulting in increased respiratory performance.

FIG. 3C illustrates a portion of connector 70 in engagement with tooth 62 selected from tooth 500f, 500g, 500h, 500i. As illustrated in FIG. 3C, side 73 of connector 70 is oriented labially, and side 71 of connector 70 is oriented lingually to be in biased engagement with labial side 64 of tooth 62, tip 69 of tooth 62, and a portion of lingual side 66 of tooth 62 proximate tip 69. As illustrated in FIG. 3C, anterior flange 74 may extend a distance T from the centerline of tooth 62 to posterior end 75 of anterior flange 74. Anterior flange 74 defines sides 78, 79, and channel 81 is defined by side 78 to receive one or more teeth, such as tooth 62, as illustrated. In various implementations, T may generally range from about 10 mm to about 30 mm. In various implementations, T may be about 12 mm. In various implementations, T may be either constant or may vary along the length of anterior flange 74.

Anterior flange 74 engages tongue tip 113 in various ways to stimulate the hypoglossal nerve. As illustrated, tongue tip 113 of tongue 100 is in contact with posterior end 75 of anterior flange 74 and with side 78 of anterior flange 74, which may cause positioning of the tongue down and anteriorly resulting in dilation of the pharyngeal airway and concomitant increased respiratory performance.

Figure 4A:
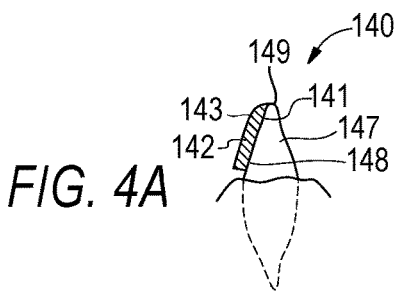
FIG. 4A illustrates by cross-sectional view another exemplary implementation of a dental appliance in engagement with an anterior mandibular tooth.

FIG. 4A illustrates a portion of connector 142 of exemplary dental appliance 140 in engagement with, for example, tooth 147 selected from tooth 500e, 500f, 500g, 500h, 500i, 500j. Side 141 of connector 142 is biased against labial side 148 of tooth 147 to the tip 149 of tooth 147, in this implementation, with tip 149 not covered by connector 142.

Figure 4B:
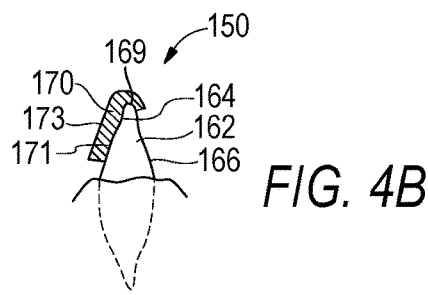
FIG. 4B illustrates by cross-sectional view yet another exemplary implementation of a dental appliance in engagement with an anterior mandibular tooth.

FIG. 4B illustrates an implementation of dental appliance 150 including a portion of connector 170 in engagement with, for example, tooth 162 selected from tooth 500e, 500f, 500g, 500h, 500i, 500j. As illustrated in FIG. 4B, side 173 of connector 170 is oriented labially, and side 171 of connector 170 is in biased engagement with labial side 164 of tooth 162, tip 169 of tooth 162, and a portion of lingual side 166 of tooth 162 proximate tip 169. Accordingly, tip 169 of tooth 162 is covered by connector 170, in this implementation.

Figure 5A:
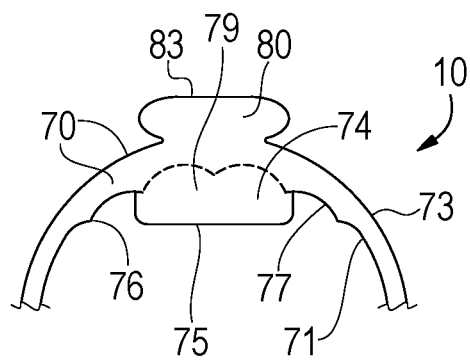
FIG. 5A illustrates by top view portions of the exemplary implementation of the dental appliance of FIG. 1A.
Figure 5B:
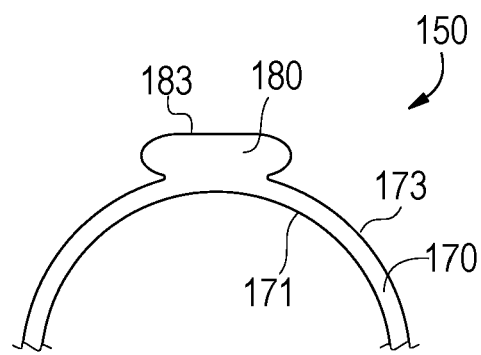
FIG. 5B illustrates by top view portions of an exemplary implementation of a dental appliance.
Figure 5C:
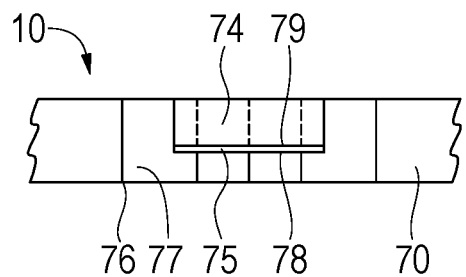
FIG. 5C illustrates by frontal view portions of the exemplary implementation of the dental appliance of FIG. 1A.

FIGS. 5A and 5C illustrates connector 70. Side 71 of connector 70, which is biased against labial sides of anterior mandibular teeth, such as tooth 107, conforms to the shapes of the anterior mandibular teeth, in this implementation. As illustrated, side 71 of connector 70 includes recesses 77 within which sides of the anterior mandibular teeth are received, such as labial side 108 of tooth 107, and side 71 of connector 70 includes crests 76 that intrude into interstices between teeth. As illustrated in FIG. 5C, connector 70 is of generally constant width along its length. Anterior flange 74 including posterior end 75 extends along mesial portions of connector 70, as illustrated. Anterior flange 74 may extend posteriorly along connector 70 to a greater or lesser extent, in various other implementations.

Figure 5D:
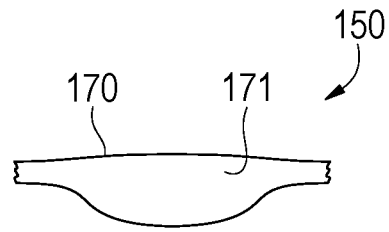
FIG. 5D illustrates by frontal view portions of the exemplary implementation of FIG. 5B.

FIGS. 5B and 5D illustrates connector 170 of dental appliance 150. Side 171 of connector 170, which is biased against labial sides of anterior mandibular teeth, such labial side 164 of tooth 162, is generally smooth so as not to conforms to the specific shapes of the anterior mandibular teeth, in this implementation. As illustrated in FIG. 5C, connector 170 is of varying width along its length that generally conforms to the shape of labial anterior portions of the user's mouth.

Figure 6A:
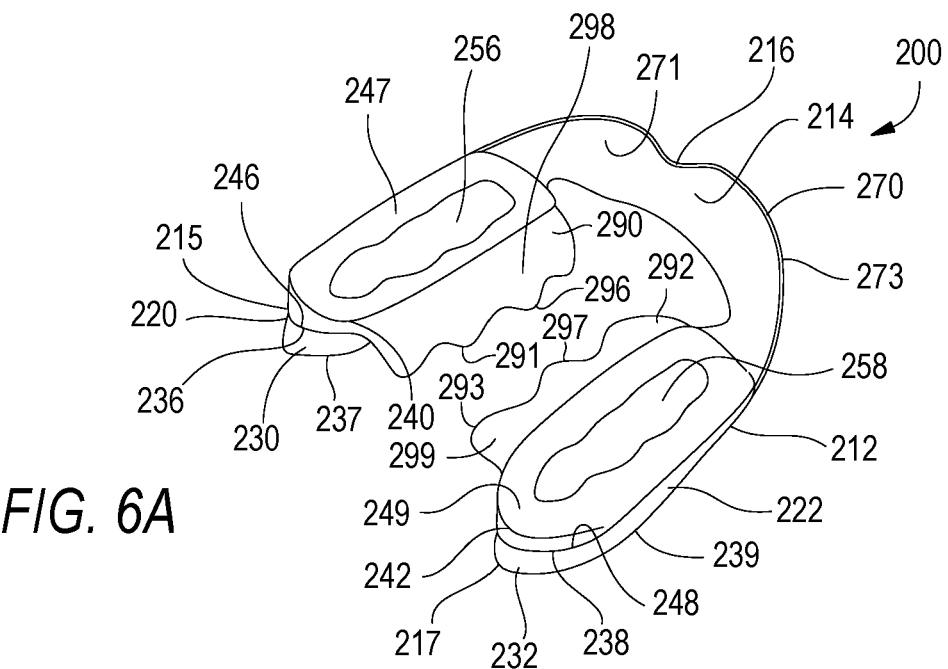
FIG. 6A illustrates by top rear perspective view an exemplary implementation of a dental appliance.
Figure 6B:
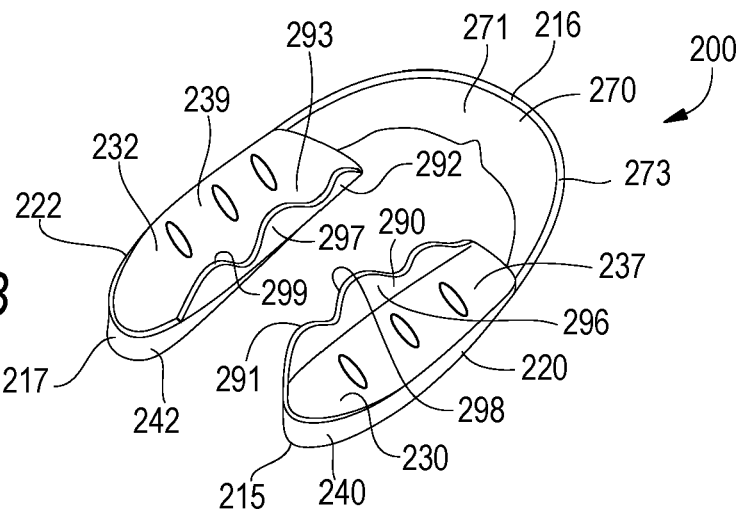
FIG. 6B illustrates by bottom rear perspective view the exemplary implementation of the dental appliance of FIG. 6A.
Figure 6C:
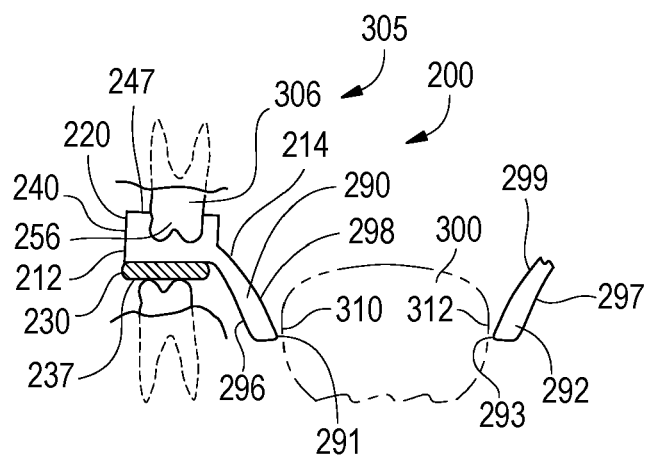
FIG. 6C illustrates by cross-sectional view the exemplary implementation of the dental appliance of FIG. 6A.

FIGS. 6A, 6B, and 6C illustrate an exemplary implementation of a dental appliance 200. The dental appliance 200, as illustrated in FIGS. 6A and 6B, is formed as a generally U-shaped member, the curved portions of the "U" extends around anterior portions of the user's mouth and the straight portions of the "U" extend from the anterior toward the posterior of the mouth. Dental appliance 200 defines a buccal-labial side 212 that is generally oriented toward the cheeks and/or lips of the user and a lingual side 214 that is generally oriented toward the user's tongue 300 when the dental appliance 200 is positioned in the mouth. As illustrated in FIGS. 6A, 6B and 6C, exemplary dental appliance 200 includes bodies 220, 222 connected to one another by connector 270. Anterior segment 216 of dental appliance 200 is positioned anteriorly and posterior ends 215, 217 are positioned posteriorly mesially symmetrically with respect to one another in the mouth when dental appliance 200 is received in the mouth of the user, in this implementation.

As illustrated in FIGS. 6A and 6B, bodies 220, 222 of exemplary dental appliance 200 include occlusal pads 240, 242 bonded to bite pads 230, 232, respectively. As illustrated, side 246 of occlusal pad 240 is bonded to side 236 of bite pad 230, and side 248 of occlusal pad 242 is bonded to side 238 of bite pad 232. Sides 236, 238, of bite pads 230, 232 are generally oriented opposite to sides 237, 239 of bite pads 230, 232, respectively, and sides 246, 248 of occlusal pads 240, 242 are generally oriented opposite to sides 247, 249 of occlusal pads 240, 242, in this implementation.

In the implementation of FIGS. 6A and 6B, occlusal pads 240, 242 define occlusal pad channels 256, 258 in sides 247, 249, respectively. Occlusal pad channels 256, 258 may removably engage posterior maxillary teeth on opposing sides of the maxillae to removably attach dental appliance 200 to the maxillary teeth. For example, occlusal pad channels 256, 258 of dental appliance 200 may engage the maxillary Pt bicuspid, maxillary 2nd bicuspid, maxillary 1" molar, maxillary 2nd molar, and maxillary $3^{rd}$ molar (when present) on the left side and right side, respectively. Occlusal pad channels 256, 258 may be fit to the users teeth in order to conform to the shape of the users teeth including interstices between the user's teeth. The dental appliance may be removably attached to various maxillary teeth, in various implementations.

When occlusal pad cannels 256, 258 of occlusal pads 240, 242 are engaged with maxillary teeth, sides 247, 249 of occlusal pads 240, 242 are oriented toward the maxillary gums and sides 237, 239 of bite pads 230, 232 are oriented toward the mandibular teeth. The mandibular teeth may engage with sides 237, 239 of bodies 220, 222, respectively, which may include treads and so forth, and may otherwise be generally adapted to engage the mandibular teeth.

As illustrated in FIGS. 6A and 6B, body 220 and body 222 are connected to one another by connector 270. Side 271 of connector 270 is oriented lingually and side 273 of connector 270 is oriented buccal labially, as illustrated, when dental appliance 200 is positioned in the mouth. Connector 270 generally passes about buccal-labial portions of the anterior maxillary teeth of the user with side 271 of connector 270 biased variously against the anterior maxillary teeth and anterior maxillary gums, and side 273 of connector 270 is oriented labially (i.e. toward the lips), in this implementation.

As illustrated in FIGS. 6A, 6B, flanges 290, 292 extend forth in lingual mesial directions from lingual side 214 of dental appliance 200 generally along the straight portions of the "U," as illustrated in FIGS. 6A and 6B. Flange 290 extends lingually toward the mandible from body 220 with edge 291 of flange 290 being of a scalloped configuration, as illustrated. Similarly, as illustrated, flange 292 extends lingually toward the mandible from body 222 with edge 293 of flange 292 being of a scalloped configuration. When exemplary implementation of dental appliance 200 is engaged with the maxillary teeth, sides 298, 299 of flanges 290, 292 are oriented generally toward the palate while avoiding contact with the palate, while sides 296, 297 of flanges 290, 292 are oriented toward the mandible while avoiding contact with the lingual frenulum root of the tongue, or other anatomical structures axially below the side of the tongue.

In various implementations, flanges 290, 292 may be of unitary construction with the occlusal pads 240, 242, so that flanges 290, 292 are formed of the same material as occlusal pads 240, 242. In various implementations, flanges 290, 292 may be of unitary construction with the bite pads 230, 232, so that flanges 290, 292 are formed of the same material as bite pads 230, 232. Flanges 290, 292 may extend forth from various portions of lingual side 214 of dental appliance 200 including various portions of body 220, 222, in various implementations.

As illustrated in FIG. 6C, body 220 of dental appliance 200 is engaged with maxillary tooth 306, where maxillary tooth 306 may be selected from maxillary teeth 305 including maxillary 1st bicuspid, maxillary 2'd bicuspid, maxillary 1st molar, maxillary 2'd molar, and maxillary $3^{rd}$ molar (when present) on the left side. Mandibular tooth 216, as illustrated, is biased against side 237 of bite pad 230, and mandibular tooth 216 is opposite maxillary tooth 306. Mandibular tooth may be, for example, one of 500a, 500b, 500c, 500d (see FIG. 2). As illustrated in FIG. 6C, body 220 includes bite pad 230, occlusal pad 240, and flange 290. Bite pad 230 is secured to occlusal pad 240, and maxillary tooth 306 is received in occlusal channel 256 of occlusal pad 240, as illustrated.

Edge 291 of flange 290 may be biased against at least portions of side 310 of the portion of the tongue 300, for example, adjacent maxillary tooth 306. Edge 293 of flange 292 may be biased against portions of side 310 of tongue 300, as illustrated in FIG. 6C. Sides 310, 312 of tongue 300 may be generally adjacent mandibular teeth from the mandibular 1st bicuspid to the mandibular $3^{rd}$ molar (when present) along the left and right sides, respectively. The biasing of edges 291, 293 of flanges 290, 292 against at least portions of sides 310, 312, respectively, of tongue 300 may stimulate the hypoglossal nerve causing contraction of the genioglossus so that the tongue is positioned anteriorly and lowered toward the mandible, which may result in dilation of the pharyngeal airway and, thus, increased respiratory performance.

Figure 7A:
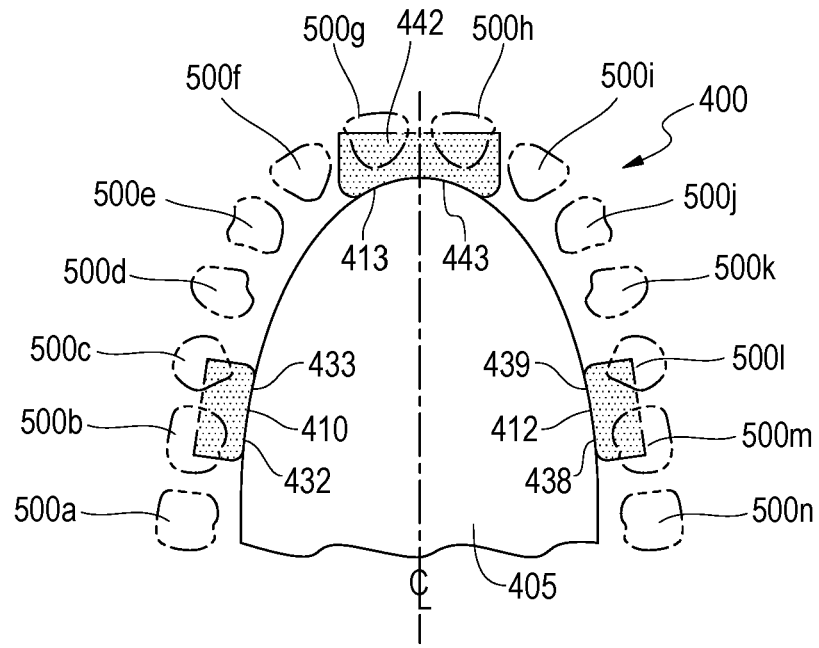
FIG. 7A illustrates by plan view portions of an exemplary implementation of a dental apparatus in engagement with a mouth.
Figure 7B:
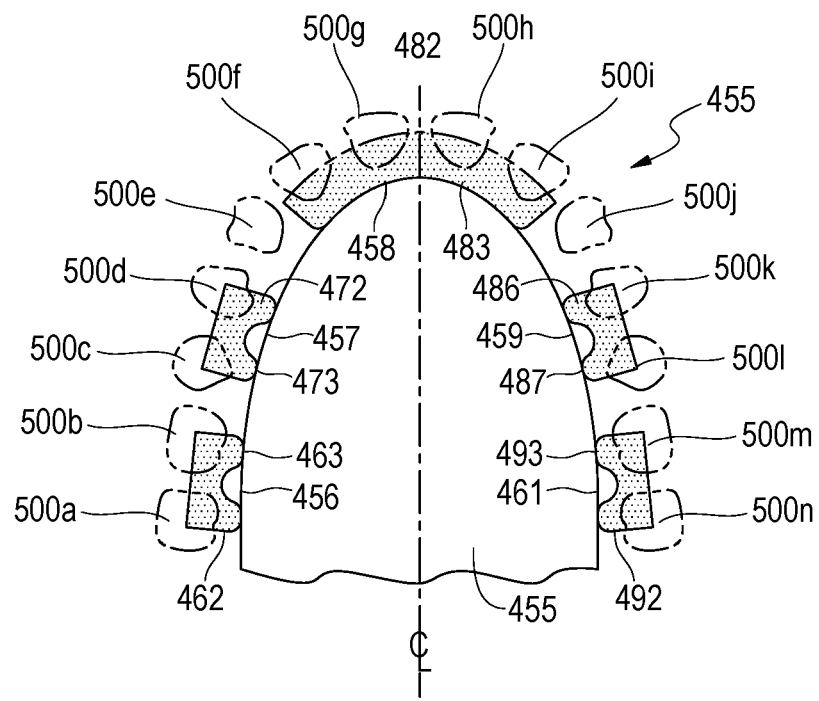
FIG. 7B illustrates by plan view portions of another exemplary implementation of a dental apparatus in engagement with a mouth.

FIGS. 7A and 7B illustrated implementations of dental appliances 400, 450 having various exemplary arrangements of flanges 432, 442, 462, 472, 482 that interact with the tongue, inter cilia, to stimulate the hypoglossal nerve in order to cause forward contraction of the genioglossus that may result in an increased oropharynx opening in the throat. Other arrangements or numbers of flanges, such as flanges 74, 90, 92, 290, 292, 432, 442, 462, 472, 482, may be disposed in various ways about the dental appliance, for example, to stimulate the hypoglossal nerve of the tongue at various locations by contacting the tongue in order to prompt forward contraction of the genioglossus, in various implementations.

FIG. 7A illustrates portions of dental appliance 400 including flange 432 with edge 433, flange 438 with flange 439, and flange 442 with edge 443. Flanges 432, 438, 442 are connected with other structures of dental appliance 400 that have been omitted from FIG. 7A for clarity of explanation. As illustrated in FIG. 7A, edge 433 of flange 432 biases against side 410 of tongue 405 to stimulate the hypoglossal nerve generally proximate teeth 500b, 500c. Edge 439 of flange 438 biases against side 412 of tongue 405 to stimulate the hypoglossal nerve, as illustrated, generally proximate teeth 5001, 500m. Edge 443 of flange 442 biases against tongue tip 413 of tongue 405 generally proximate teeth 500g, 500h (the mandibular central incisors) to stimulate the hypoglossal nerve. Note that edges 433, 439, 443 have a curvature that conforms generally to the corresponding curvature of the tongue.

FIG. 7B illustrates portions of dental appliance 450 including flange 462 with edge 463, flange 472 with edge 473, flange 482 with edge 483, flange 486 with edge 487, and flange 492 with edge 493. As illustrated, flanges 462, 472, 482 486, 492 are connected with other structures of dental appliance 450 that have been omitted from FIG. 7B for clarity of explanation. Edges 463, 473, 487, 493 of flanges 462, 472, 486, 492 bias against corresponding sides 456, 457, 459, 461 of tongue 455 to stimulate the hypoglossal nerve at these locations, and edge 483 of flange 482 biases against tongue tip 458 to stimulate the hypoglossal nerve proximate tongue tip 458. Side 456 is proximate teeth 500a, 500b, side 457 is proximate teeth 500c, 500d, side 458 is proximate teeth 500f, 500g, 500h, 500i, side 459 is proximate teeth 500k, 5001, and side 461 is proximate teeth 500m, 500n, as illustrated. Flanges 462 and 472 are, for example, in spaced relation to one another as are flanges 486, 492, in this implementation. Note that edges 463, 473, 487, 493 have a concave shape so that only portions of edges 463, 473, 487, 493 contact tongue 455, in this implementation.

Figure 9:
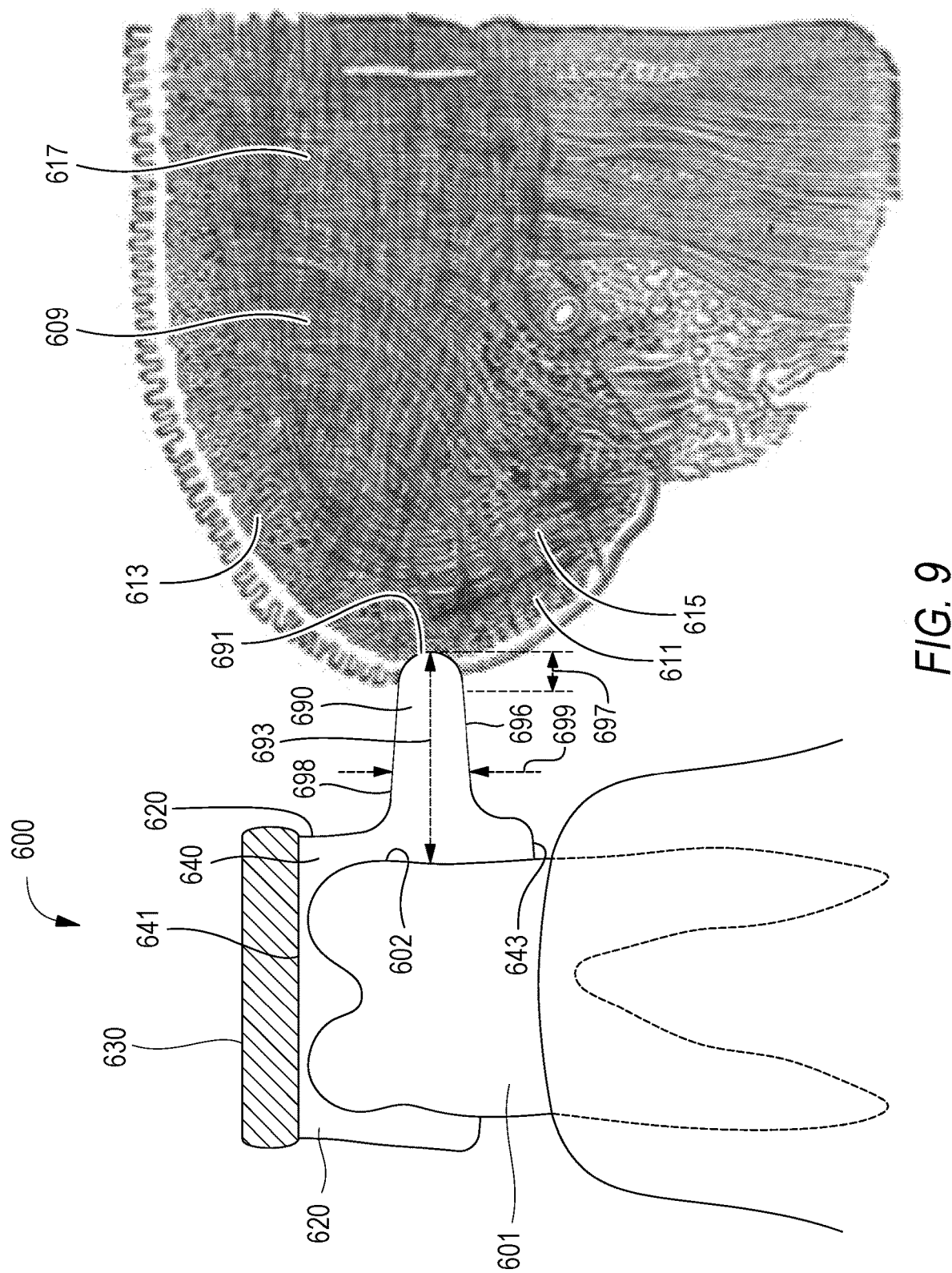
FIG. 9 illustrates by side cross-sectional view an exemplary implementation of a dental apparatus in engagement with the mouth, the dental appliance in communication with the tongue, features of the anatomy of the tongue being illustrated in cross-section at a location along the anterior-posterior direction, the cross-section being perpendicular to the anterior-posterior direction.

FIG. 9 illustrates portions of dental appliance 600 including base 620 attached removably to tooth 601, with tooth 601 being a mandibular tooth selected, for example, from 500a, 500b, 500c, 500d. Flange 690, as illustrated in FIG. 9, extends forth from lingual side of dental appliance by length 693 to impress edge 691 of flange 690 into tongue 609 a length 697. Length 693 is measured from lingual side 602 of tooth 601 to edge 691 of flange 690, as illustrated. Length 697, as illustrated, may be sufficient to compress the transversus linguae 613, the styoglossus 611, or both the transversus linguae 613 and the styoglossus 611 that, in turn, causes forward contraction of the genioglossus 617. Tongue 609 is illustrated in cross-section at a location along the along the anterior-posterior dimension. Depending upon the anterior-posterior positioning of flange 690, edge 691 may impress into the hyoglossus. 615 a length, such as length 697, sufficient to compress the hyoglossus 615 that, in turn, causes forward contraction of the genioglossus 617. Note that the hypoglossal nerve innervates the transversus linguae 613, the styoglossus 611, the hyoglossus, 615 and the genioglossus 617, so that the transversus linguae 613, the styoglossus 611, the hyoglossus 615, and the genioglossus 617 communicate with one another via the hypoglossal nerve and by physical interconnections, as illustrated in FIG. 9. Accordingly, impressment of flange 690 onto one or more of the transversus linguae 613, the styoglossus 611, the hyoglossus 615, and the genioglossus 617 may cause positioning of the tongue down and anteriorly resulting in dilation of the pharyngeal airway and concomitant increased respiratory performance. The flange 690 has length, such as length 693, to impress into one or more of the transversus linguae 613, the styoglossus 611, the hyoglossus 615, and the genioglossus 617 to cause positioning of the tongue down and anteriorly resulting in dilation of the pharyngeal airway and concomitant increased respiratory performance, in various implementations.

As illustrated in FIG. 9, base 620 includes bite pad 630 and occlusal pad 640 bonded to one another. Flange 690 is formed unitarily with occlusal pad 640, in this implementation. The length 699 between sides 696, 698 is greatest where flange 690 emerges from occlusal pad 640 gradually diminishing toward edge 691 with edge 691 being rounded. Flange 690 has a bell shape, in this implementation. Other implementations of the flange, such as flange 690, may be bell shaped and skewed. Still other implementation of the flange, such as flange 690, may have a constant length between sides, such as length 699, to have a generally constant cross-sectional shape such as a rectangular cross-sectional shape. Length 699 is less than the length between side 641 and side 643 of occlusal pad 640, as illustrated.

Experiment 1

Various commercially available dental appliances and modifications of the commercially available dental appliances were tested in vivo in Experiment 1. These tests are labeled R1-R5 and are described as follows:

R1—No dental appliance
R2—Wedge mouthpiece with reverse 4 mm in the back of mouth and 2 mm in the front, inside portion is missing, no contact with the tongue
R3—Under Armour® boil and bite
R4—Altered Under Armour® boil and bite with the inside portion missing, no contact with the tongue
R5—Similar to R2 with a reverse 4 mm in the back of the mouth and 2 mm in the front and instead of a slope there is a noticeable 1 mm step in the middle of the increase from front to back, lingual portion of dental appliance is missing, no contact with the tongue.

Two exemplary configurations of the dental apparatus according to the present disclosure were tested in vivo in Experiment 1. These are labeled and described as follows:

DG proto*—generally similar to the exemplary dental appliance 10 including flanges 90, 92 generally posterior on dental appliance 10. Does not include anterior flange 74.
DG tong*—generally similar to the exemplary dental appliance 10 including flanges 90, 92 generally located on posterior portions of dental appliance 10. Includes anterior flange 74 that may push the tongue down slightly thereby placing the tongue in optimal position to increase airway opening.

* the numbers 1 & 2 refer to specific tests.

In Experiment 1, the subject ran 5 minutes on a treadmill with the dental appliance inserted in the subject's mouth. Then, the respiratory rate of the subject was measured using a True Max metabolic cart manufactured by Parvo Medics, Inc., Sandy, Utah immediately following the 5 minute run on the treadmill, The same subject tested each of the dental appliances. The tests occurred on different days, so that the subject had sufficient time to recover physically between tests. The subject was, of course, in good physical condition. Results for the various dental appliances are illustrated in FIG. 8

Figure 8:
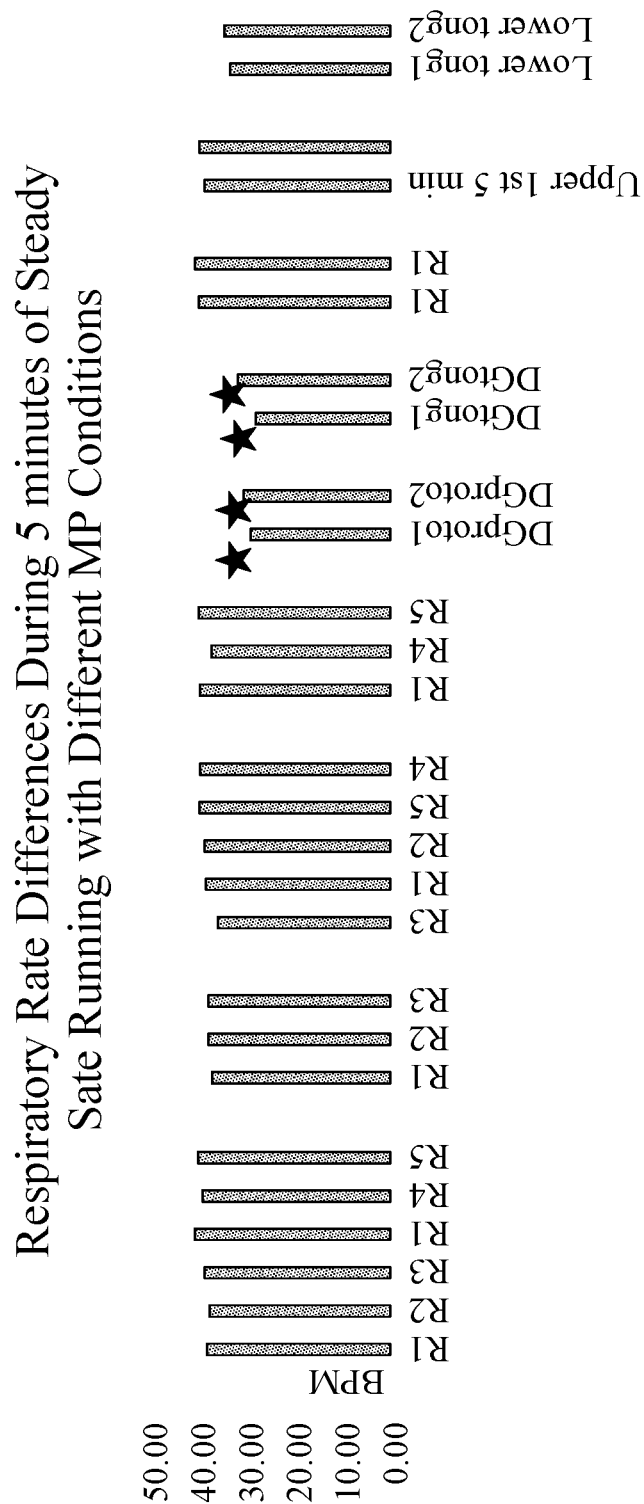
FIG. 8 illustrates by bar graph experimental results from Experiment 1.

As illustrated in FIG. 8, the measured respiratory rates for the subject using dental appliances R1-R5 ranged from about 38 BPM to about 42 BPM (Breaths Per Minute). The measured respiratory rate for the subject using dental appliance DG prototype were 29.8 BPM and 31.3 BPM. The measured respiratory rate for the subject using dental appliance DG tong were 28.6 BPM and 32.3 BPM.

Thus, these experimental results indicate that respiratory rate decreased by as much as 13 BPM when dental appliances DG prototype and DG tong were used by the subject from the respiratory rates exhibited when the subject either used no dental appliances R1 or when the subject used dental appliances R2-R5. The decrease in respiratory rate using dental appliances DG prototype and DG tong is indicative of increased respiratory performance resulting from use of dental appliances DG prototype and DG tong.

In operation, the dental appliance, such as dental appliance 10, 140, 150, 200, 450, may be received in the mouth of the user in removable attachment to one or more teeth, such as tooth 500a, 500b, 500c, 500d, 500k, 5001, 500m, 500n, or various maxillary teeth such as maxillary molars and maxillary bicuspids. The dental appliance may be removably attached to various combinations of teeth in various implementations.

With the dental appliance removably attached within the mouth of a user, one or more flanges, such as flange 74, 90, 92, 290, 292, 432, 438, 442, 462, 472, 482, 486, 492, 690 may contact the tongue, such as tongue 100, 300, 405, 455, 609 to stimulate the hypoglossal nerve of the tongue at various locations in order to prompt forward contraction of the genioglossus. Forward contraction of the genioglossus may result in dilation of the pharyngeal airway and concomitant increased respiratory performance. The hypoglossal nerve may be stimulated at various locations around the tongue including the side of the tongue and proximate the tip of the tongue, and flanges may be provided at various locations about the dental appliance to so stimulate the hypoglossal nerve by contact with the tongue.

A bumper, such as bumper 80, may stimulate the lip or lips to provoke pursed lip breathing that may increase respiratory performance. Wedge shaped bite pads, such as bite pads 30, 32, may position the jaw in ways that increase respiratory performance.

Various stimulations of the lips, the hypoglossal nerve, positioning of the jaw, and combinations thereof by the dental appliance may increase respiratory performance by other as yet unrecognized physiologic responses.

The foregoing discussion along with the Figures discloses and describes various exemplary implementations. These implementations are not meant to limit the scope of coverage, but, instead, to assist in understanding the context of the language used in this specification and in the claims. The Abstract is presented to meet requirements of 37 C.F.R. § 1.72(b) only. This Abstract is not intended to identify key elements of the apparatus and methods disclosed herein or to delineate the scope of this disclosure. Upon study of this disclosure and the exemplary implementations herein, one of ordinary skill in the art may readily recognize that various changes, modifications and variations can be made thereto without departing from the spirit and scope of the inventions as defined in the following claims.

The invention claimed is:

1. A dental appliance, comprising:
   a first occlusal pad and a second occlusal pad;
   a connector that extends between said first occlusal pad and said second occlusal pad, said connector being curved;
   a lingual side of each of said occlusal pads, each of said lingual sides oriented toward a mesial centerline of said dental appliance;
   a flange disposed at a center of said connector on a surface and said flange extending in a posterior direction and configured to engage a tip of a user's tongue to move the tongue forward and downward.

2. The dental appliance of claim 1, said first occlusal pad and said second occlusal pad each having a bite pad.

3. The dental appliance of claim 2, each of said bite pad being sloped.

4. The dental appliance of claim 1, further comprising a flange extending from each of said lingual sides of each of said occlusal pads.

5. The dental appliance of claim 4, said flanges of said occlusal pads each having an interior edge with a plurality of curves.

6. The dental appliance of claim 4, further comprising at least one support disposed within each of said flanges.

7. The dental appliance of claim 6, said at least one support being T-shaped.

8. A dental appliance, comprising:
   a first occlusal pad and a second occlusal pad;
      a connector extending between each of said first and second occlusal pads and connected near anterior ends of each of said first and second occlusal pads;
      a flange extending from said connector in a posterior direction, said flange extending from a mesial location of said connector, said flange of said connector configured to engage a tip of a user's tongue and facilitate a change in an airway of the user.

9. The dental appliance of claim 8, further comprising an occlusal flange extending from a lingual side of each of said occlusal pads.

10. The dental appliance of claim 9, each of said occlusal flanges having an internal support formed therein.

11. The dental appliance of claim 9, further comprising a bite pad formed on each of said occlusal pads.

12. The dental appliance of claim 11, each of said bite pads having a wedge-shape.

13. The dental appliance of claim 8, said dental appliance configured to stimulate nerves of a user's tongue to improve airflow for the user.

14. A dental appliance, comprising:
   a first occlusal pad and a second occlusal pad;
   a curved connector extending between said first occlusal pad and said second occlusal pad;
   a connector flange centrally disposed on said curved connector and extending in a posterior direction from said curved connector;
   a first occlusal flange extending in a mesial direction from said first occlusal pad and a second occlusal flange extending from said second occlusal pad in a mesial direction;
   each of said first and second occlusal flanges having a curved innermost edge; and,
   a support disposed within each of said first and second occlusal flanges.

15. The dental appliance of claim 14, said first and second occlusal pads having an inclined upper surface.

16. The dental appliance of claim 15, said inclined upper surface configured to shift a mandible of the user anteriorly.

17. The dental appliance of claim 14, further comprising a first bite pad and a second bite pad formed respectively on said first and second occlusal pads.

18. The dental appliance of claim 14 wherein nerves of a user's tongue are stimulated to prompt forward contraction of the tongue and dilate a pharyngeal airway.

* * * * *